United States Patent [19]

Hayano et al.

[11] Patent Number: 5,436,464
[45] Date of Patent: Jul. 25, 1995

[54] FOREIGN PARTICLE INSPECTING METHOD AND APPARATUS WITH CORRECTION FOR PELLICLE TRANSMITTANCE

[75] Inventors: Fuminori Hayano, Tokyo; Hideyuki Tashiro, Yokohama; Tsuneyuki Hagiwara; Hajime Moriya, both of Tokyo, all of Japan

[73] Assignee: Nikon Corporation, Tokyo, Japan

[21] Appl. No.: 44,197

[22] Filed: Apr. 8, 1993

[30] Foreign Application Priority Data

| Apr. 13, 1992 | [JP] | Japan | 4-118455 |
| Jun. 8, 1992 | [JP] | Japan | 4-173782 |
| Jun. 19, 1992 | [JP] | Japan | 4-161247 |

[51] Int. Cl.⁶ ............................................. G01N 21/88
[52] U.S. Cl. ............................ 250/559.01; 250/225; 356/237
[58] Field of Search ............... 250/571, 572, 559, 562, 250/563, 225; 356/237, 239, 338, 430, 431

[56] References Cited

U.S. PATENT DOCUMENTS

| Re. 33,991 | 7/1992 | Shiba et al. | 250/572 |
| 4,468,120 | 8/1984 | Tanimoto et al. | 356/237 |
| 4,669,875 | 6/1987 | Shiba et al. | 250/572 |
| 4,795,911 | 1/1989 | Kohno et al. | 250/572 |
| 4,889,998 | 12/1989 | Hayano et al. | 250/563 |
| 4,999,510 | 3/1991 | Hayano et al. | 250/571 |

FOREIGN PATENT DOCUMENTS 63-118640  5/1988  Japan.

*Primary Examiner*—David C. Nelms
*Assistant Examiner*—John R. Lee
*Attorney, Agent, or Firm*—Shapiro and Shapiro

[57] ABSTRACT

In a foreign particle inspecting method and apparatus in which a polarized beam is applied to a surface to be inspected through a light transmitting member mounted thereon, in which scattered light from a foreign particle on the surface to be inspected is received by a light receiving device through the light transmitting member, and in which the foreign particle is discriminated based on a detection signal from the light receiving device, the detection signal is corrected in conformity with the transmittance of the light transmitting member for polarized incident scanning light and the transmittance of the light transmitting member for non-polarized light scattered from the foreign particle, for various angles of incidence of the polarized light and emergence of the non-polarized light. Foreign particle data may be indicated by a mapping method.

14 Claims, 12 Drawing Sheets

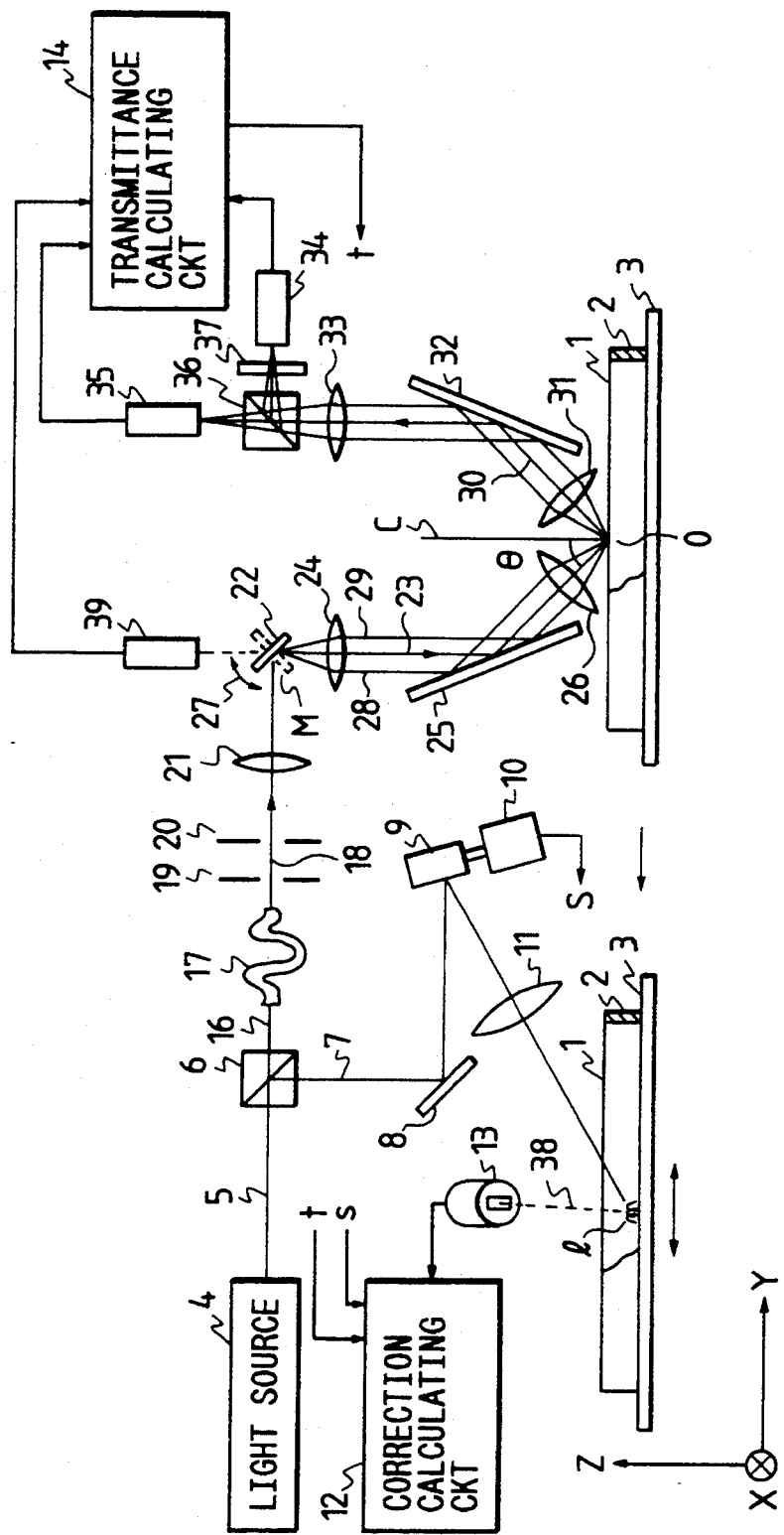

A : 1
B : 0
C : 2

FOREIGN PARTICLE INSPECTING METHOD AND APPARATUS WITH CORRECTION FOR PELLICLE TRANSMITTANCE

BACKGROUND OF THE INVENTION

1. Field of the Invention

This invention relates to a foreign particle inspecting apparatus, a foreign particle inspecting method and a foreign particle data indicating method, and particularly to a foreign particle inspecting apparatus, a foreign particle inspecting method and a foreign particle data indicating method for foreign particles on a substrate such as a reticle or a photo-mask used in a semiconductor manufacturing process or a liquid crystal display element manufacturing process.

2. Related Background Art

In manufacturing a semiconductive integrated circuit or a liquid crystal display element by the use of the photography technique, use is made of a reticle or a photo-mask (hereinafter generically referred to as the "reticle") on which is formed a pattern to be transferred onto a wafer having photo-resist applied thereto. If in the manufacturing process, a foreign particle such as dust adheres to the pattern area of the reticle, there will occur a defect common to all chips of the wafer onto which the pattern of the reticle is transferred. Therefore, in the manufacturing process, it is necessary to strictly inspect the presence or absence of any foreign particle on the pattern area of the reticle. Thus, as an apparatus for automatically inspecting any foreign particle adhering to the surface of an object to be inspected, use has heretofore been made of a foreign particle inspecting apparatus which two-dimensionally scans the surface of the object to be inspected by a light beam from a predetermined light source, and detects scattered light from a foreign particle on that surface to thereby detect the foreign particle. Such an apparatus is disclosed in U.S. Pat. No. 4,468,120.

Also, in recent times, there are cases where a light transmitting thin film (hereinafter referred to as the "pellicle") is mounted on the surface of the reticle through a support frame to reduce the influence of any foreign particle. The pellicle is for preventing the adherence of any foreign particle onto the surface of the reticle. Again for the reticle thus covered with the pellicle, it is necessary to inspect the presence or absence of any foreign particle on the reticle because a foreign particle or particles may adhere to the surface of the reticle during the mounting of the pellicle.

However, with the pellicle mounted on the reticle, the light beam cannot be applied to the reticle from a low position due to the presence of the support frame for the pellicle and further, scattered light from a foreign particle cannot be received at a low angle. Therefore, with the pellicle remaining mounted on the reticle, foreign particle inspection cannot be accomplished well. In this regard, a foreign particle inspecting apparatus which can well accomplish the detection of any foreign particle on a reticle on which a pellicle is mounted is disclosed in Japanese Laid-Open Patent Application No. 63-118640.

Also, when foreign particle detection is to be effected for a surface to be inspected on which a pellicle is mounted, inspecting light is caused to impinge on the surface to be inspected through the pellicle and scattered light from any foreign particle on the surface to be inspected enters a detecting optical system again through the pellicle. When the transmittance of the pellicle for incident light is Ti (hereinafter referred to as the "incident light transmittance Ti") and the transmittance of the pellicle for the scattered light from the foreign particle is Ts (hereinafter referred to as the "scattered light transmittance Ts"), to equally discriminate between the size of the foreign particle on the surface to be inspected on which the pellicle is mounted and the same degree of size of a foreign particle on a surface to be inspected on which no pellicle is mounted, it is necessary that the detection signal by the foreign particle on the surface to be inspected on which the pellicle is mounted be corrected to $1/Ti \cdot Ts$ times.

Also, generally, the angle of incidence of a light beam onto the pellicle varies when the scanning position of the light beam on the surface of the reticle to be inspected varies. Also, when the scanning position of the light beam varies, the angle at which the scattered light from the foreign particle, scattered light travelling toward a detector, is incident on the pellicle, in other words, the angle of incidence of a detection optical axis determined by the positional relationship between the scanning position of the light beam and the detecting optical system (hereinafter referred to as the "angle of emergence"), varies. Therefore, by the variation in the angle of incidence, the transmittance of the pellicle for the light beam is varied, and by the variation in the angle of emergence, the transmittance of the pellicle for the scattered light from the foreign particle is varied. The detection sensitivity for the foreign particle is also varied by the variation in the transmittance of the pellicle for the light beam, and the detection sensitivity for the foreign particle is also varied by the variation in the transmittance of the pellicle for the scattered light from the foreign particle. Particularly when the thickness of the pellicle is of the order of the wavelength of the light beam and the light beam is monochromatic light, the wavelength selectivity by the thickness of the pellicle is added, and the transmittance of the pellicle for the light beam is greatly varied by the variation in the angle of incidence, and the transmittance of the pellicle for the scattered light from the foreign particle is greatly varied by the variation in the angle of emergence. In other words, even for a foreign particle of the same degree of size on the same surface to be inspected on which the pellicle is mounted, if it adheres to a different scanning position, the magnitude of the detection signal will differ.

So, U.S. Pat. No. 4,889,998 discloses a method of predetermining the transmittance of a pellicle for a light beam and the transmittance of the pellicle for scattered light from a foreign particle, with respect to each scanning position on a surface to be inspected, and correcting the magnitude of a detection signal in conformity with the scanning position of the light beam, and discloses a foreign particle inspecting apparatus for correcting any variation in the detection sensitivity for the foreign particle attributable to a variation in the transmittance of the pellicle for the light beam.

In the foreign particle inspecting apparatus, a laser beam is often used as a light source, and generally the laser beam used often has a particular direction of polarization.

Also, by making the direction of polarization of a polarized beam particular relative to a surface to be inspected, the detection signal by a foreign particle can be intensified relative to the detection signal by a circuit pattern on the surface to be inspected and therefore, in some cases, a polarized laser is positively used for foreign particle inspection with a view to make the presence of a foreign particle on the surface to be inspected conspicuous.

As described above, in the foreign particle inspecting apparatus, foreign particle inspection is often done by the use of a polarized beam, and in the apparatus disclosed in U.S. Pat. No. 4,889,998, the transmittance measured with inspecting light (a polarized beam) caused to impinge on a pellicle is regarded as the transmittance of scattered light from a foreign particle and the magnitude of the detection signal of the scatterd light is corrected.

However, even when a foreign particle is irradiated with a polarized beam, the scattered light by the irregular reflecting surface of the foreign particle has its polarized state destroyed, and the transmittance of the pellicle for the polarized beam at the same angle of incidence (the angle of incidence and the angle of emergence are the same) and the transmittance of the pellicle for the scattered light from the foreign particle whose polarized state is destroyed differ greatly from each other. Accordingly, in the prior-art foreign particle inspecting apparatus disclosed in U.S. Pat. No. 4,889,998, the error of the magnitude of the detection signal corresponding to the size of the foreign particle on the surface to be inspected is enlarged (any variation in the detection sensitivity for the foreign particle by the influence of the transmittance of the pellicle for the scattered light becomes unable to be accurately detected) and it becomes impossible to equally discriminate between the size of the foreign particle on the surface to be inspected on which the pellicle is mounted and the same degree of size of a foreign particle on a surface to be inspected on which no pellicle is mounted, or to accurately detect the same degree of foreign particle adhering to a different scanning position on the same surface to be inspected.

Further, the prior-art foreign particle inspecting apparatus has the following inconvenience.

Heretofore, the correction of foreign particle detection sensitivity has been effected by the use of the data of the pellicle transmittance preknown for the same pellicles, but even for the same pellicles, the transmittance differs greatly in some cases due to the difference in film thickness within the manufacturing tolerance. Therefore, it is necessary to calculate the transmittance by the use of the actual film thickness data of each pellicle, in addition to the average transmittance data of the pellicles, but it will increase the burden of the pellicle manufacturer to demand the actual film thickness data of each pellicle of the pellicle manufacturer, and it is not always possible to accurately calculate the transmittance of each pellicle. Accordingly, it is not realistic to pre-calculate the data of the transmittance of each pellicle.

In contrast, there has also been proposed a method of providing a transmittance measuring portion for actually measuring the transmittance of each pellicle, discretely from a foreign particle inspecting portion. In this case, it is difficult to measure the transmittance of the pellicle by just the same system as the foreign particle inspecting portion and generally, a system for measuring the transmittance by a simplified construction is incorporated as the transmittance measuring portion. However, in some cases, a correction error of transmittance arises from the difference in construction between the foreign particle inspecting portion and the transmittance measuring portion, but no consideration has heretofore been given to such a correction error.

Also, in the prior-art foreign particle inspecting apparatus, it is generally practiced to map-display the result of the detection of foreign particles (the number and sizes of foreign particles).

Specifically, as shown, for example, in FIG. 16 of the accompanying drawings, display has been made divisionally for each magnitude of the number (rank) of foreign particles. Particularly in the map display, the largest foreign particle has been displayed when a plurality of foreign particles exist within one and the same section. In FIG. 16, a map 4m indicates the locations and sizes of detected foreign particles. The size of the sections in the map 4m indicates sections of a predetermined size (e.g. 1 mm-several mm square) on the surface to be inspected, and the size of the largest foreign particle in these sections is rank-displayed. In the map 4m of FIG. 16, ranks A, B and C are displayed in the order of the magnitudes of ranks, and it is indicated that a foreign particle of rank A and two foreign particles of rank C have been detected. Further, in FIG. 16, the numbers of foreign particles within the display screen are indicated by ranks below the map 4m. In such a conventional indicating method, when a plurality of foreign particles exist within one and the same section, only the largest foreign particle is indicated. Therefore, the other foreign particles (foreign particles smaller than the indicated foreign particle) existing within the same section as the indicated foreign particle are not indicated, and this has led to the problem that the presence of small foreign particles cannot be confirmed. If an attempt is made to confirm the presence of such foreign particles which are not indicated, map display can be made with the size of a unit section area made smaller, but this has led to the problem that only a part of the area on the surface to be inspected is indicated or the map becomes larger. There is also a method of switching the map display for the confirmation of small foreign particles, but it takes time and labor to switch the map display each time small foreign particles are confirmed, and this is not practical.

SUMMARY OF THE INVENTION

The present invention has as an object thereof the provision of a foreign particle detecting method using, when a polarized beam is used as inspecting light, the transmittance of thin film regarded as the transmittance of thin film such as a pellicle for scattered light by a foreign particle, a foreign particle inspecting method and a foreign particle inspecting apparatus capable of accurately measuring the transmittance of thin film regarded as the transmittance of thin film such as a pellicle for scattered light by a foreign particle.

To achieve this object, a foreign particle inspecting method of applying a polarized beam to a surface to be inspected having a light transmitting member mounted thereon through said light transmitting member, receiving scattered light from a foreign particle on the surface to be inspected by light receiving means through said light transmitting member, and discriminating said foreign particle on the basis of a detection signal from said light receiving means has:

the first step of inputting the transmittance of said light transmitting member for said polarized beam conforming to the angle of incidence of said polarized beam onto said light transmitting member;

the second step of inputting the transmittance of said light transmitting member for a non-polarized beam conforming to the angle of incidence of said non-polarized beam onto said light transmitting member;

the third step of multiplying, when the angle formed between a normal to said light transmitting member at the point of intersection between a straight line extending from the scanning position of said polarized beam on said surface to be inspected toward said light receiving means and said light transmitting member and said straight line is the angle of emergence, the transmittance of said non-polarized beam at the angle of incidence of said non-polarized beam equal to said angle of emergence by a transmittance conforming to the angle of incidence of said polarized beam at the scanning position of said polarized beam on said surface to be inspected, and calculating a correction value; and the fourth step of dividing said detection signal by the correction value and correcting said detection signal.

Also, a foreign particle inspecting apparatus for inspecting any foreign particle on a surface to be inspected is provided with:

means for applying a polarized beam to said surface to be inspected having a light transmitting member mounted thereon through said light transmitting member;

light receiving means for receiving scattered light from a foreign particle on said surface to be inspected through said light transmitting member and outputting a detection signal;

discriminating means for discriminating said foreign particle on the basis of the detection signal from said light receiving means;

first measuring means for actually measuring the transmittance of said light transmitting member for said polarized beam conforming to the angle of incidence of said polarized beam onto said light transmitting member;

second measuring means for actually measuring the transmittance of said light transmitting member for a non-polarized beam conforming to the angle of incidence of said non-polarized beam onto said light transmitting member;

calculating means for multiplying, when the angle formed between a normal to said light transmitting member at the point of intersection between a straight line extending from the scanning position of said polarized beam on said surface to be inspected toward said light receiving means and said light transmitting member and said straight line is the angle of emergence, the transmittance of said non-polarized beam at the angle of incidence of said non-polarized beam equal to said angle of emergence by a transmittance conforming to the angle of incidence of said polarized beam at the scanning position of said polarized beam on said surface to be inspected, and calculating a correction value; and correcting means for dividing said detection signal by the correction value and correcting said detection signal.

In the above-described foreign particle inspecting method and foreign particle inspecting apparatus, instead of the transmittance of the light transmitting member for inspecting light (polarized beam), the transmittance of the light transmitting member for a non-polarized beam of substantially the same wavelength as the polarized beam is regarded as the transmittance of scattered light by an actual foreign particle and the correction and calculation of the detection signal are effected.

This is based on the recognition that the transmittance of the light transmitting member for the scattered light of a polarized beam scattered by the irregular reflecting surface of a foreign particle and having its polarized state destroyed is more approximate to the transmittance for a non-polarized beam of substantially the same wavelength as the polarized beam than to the transmittance for the polarized beam, and any foreign particle on the surface to be inspected having the light transmitting member mounted thereon can be detected without sensitivity irregularity.

Another embodiment of the present invention has as an object thereof the provision of a foreign particle inspecting apparatus and a foreign particle inspecting method which, when a substrate to be inspected having thin film such as a pellicle mounted thereon is scanned by a light beam to thereby detect any foreign particle, can well correct the foreign particle detection sensitivity by the transmittance of the thin film for the light beam and well detect any foreign particle without resorting to the transmittance of the thin film for the light beam.

To achieve this object, a foreign particle inspecting method of scanning by incident light the surface of a substrate to be inspected having mounted thereon a frame having light transmitting thin film applied thereto, and detecting any foreign particle adhering to said substrate to be inspected on the basis of a signal obtained by converting light information created from said substrate to be inspected uses:

a reference substrate whose surface having a standard particle attached thereto is covered with said light transmitting reference thin film through said frame, and transmittance measuring means for applying first light to an object to be inspected and measuring the reflectance of said object to be inspected to thereby measure the transmittance of said object to be inspected;

scanning means for scanning the surface of said substrate to be inspected by second light, light receiving means for receiving light information created from said substrate to be inspected and outputting a detection signal, and detecting means for detecting said foreign particle on the basis of said detection signal; and has:

the first step of measuring the transmittance of said reference thin film covering the surface of said reference substrate for said first light by the use of said transmittance measuring means;

the second step of detecting the scattered light of said second light from said standard particle attached to the surface of said reference substrate through said reference thin film by the use of said foreign particle detecting means; and the third step of correcting said detection signal on the basis of the transmittance obtained in said first step and the scattered light information obtained in said second step.

Also, a foreign particle inspecting apparatus for scanning by incident light the surface of a substrate to be inspected having mounted thereon a frame having light transmitting thin film attached thereto, and detecting any foreign particle adhering to said substrate to be inspected on the basis of a signal obtained by converting light information created from said substrate to be inspected is provided with:

applying means for applying first light to an object to be inspected;

first light receiving means for detecting the reflected light from said object to be inspected; transmittance measuring means for measuring the reflectance of said object to be inspected to thereby measure the transmittance of said object to be inspected;

detecting means having scanning means for scanning said substrate to be inspected by second light and second light receiving means for converting light information created from said substrate to be inspected into an electrical signal;

first memory means for memorizing the transmittance of predetermined reference thin film measured by said transmittance measuring means;

second memory means for memorizing a predetermined sensitivity correction value; and calculating means for multiplying the output signal of said second light receiving means of said detecting means by said sensitivity correction value memorized by said second memory means, the transmittance of said reference thin film memorized by said first memory means and the inverse number of the transmittance of the thin film covering the surface of said substrate to be inspected measured by said transmittance measuring means.

Thus, the result of the measurement of the transmittance in the transmittance measuring means and the detection signal in the foreign particle detecting means are standardized by the introduction of the reference thin film and therefore, foreign particle detection sensitivity can be accurately corrected in conformity with the transmittance of the thin film.

Also, still another embodiment of the present invention has as an object thereof to enable, when the result of the detection of foreign particles is to be indicated in a predetermined section unit, both of number indication with a predetermined section as a unit and number indication with a section smaller than the predetermined section (or the smallest indication section) as a unit to be accomplished.

To achieve this object, a foreign particle data indicating method of indicating the position and size of a foreign particle on an object to be inspected has:

a first indicating method of indicating the position and size of said foreign particle in the form of a map;

a second indicating method of number-indicating the largest foreign particle within a predetermined indicating section divisionally for each rank conforming to the size of said foreign particle and indicating the number of foreign particles within an indicating area indicated in said map; and a third indicating method of number-indicating the largest foreign particle within the smallest indicating section divisionally for each rank conforming to the size of said foreign particle and indicating the number of foreign particles within the inspectable area of said object to be inspected;

said second indicating method and said third indicating method being carried out at the same time to thereby effect both of the indication of the foreign particle within said predetermined section and the indication of the particle within said smallest indicating section.

According to this indicating method, the number of foreign particles in an indication screen can be indicated by ranks in a predetermined section unit and at the same time, the total number of foreign particles in each minimum indication section unit can be indicated by ranks. Therefore, two sets of numbers indicating the numbers of foreign particles can be compared and from the difference therebetween, whether a foreign particle smaller than the foreign particle being indicated within the predetermined section exists within the same section can be confirmed easily. Also, where the predetermined section and the indicating section are of the same unit, the degree of closeness of the predetermined section can be confirmed.

BRIEF DESCRIPTION OF THE DRAWINGS

FIG. 1 is a schematic view of a foreign particle inspecting apparatus according to a first embodiment of the present invention.

DETAILED DESCRIPTION OF THE PREFERRED EMBODIMENTS

Figure 2A:
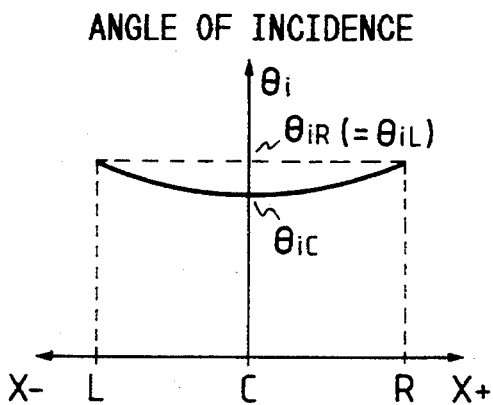
FIG. 2A shows the relation of the angle of incidence of a polarized beam to the position of incidence of the polarized beam in the apparatus of FIG. 1.

A first embodiment of the present invention will hereinafter be described with reference to the drawings. In the apparatus of FIG. 1, an actual measuring position for actually measuring transmittance is set discretely from a location at which foreign particle inspection is actually done. That is, a transmittance measuring optical system (first and second measuring means) independent of a detecting optical system for foreign particle inspection is provided.

In FIG. 1, a predetermined circuit pattern (not shown) is provided on a reticle 3, and thin film (hereinafter referred to as the "pellicle film") 1 such as a pellicle is provided at a predetermined distance from the circuit pattern above the reticle 3 with a pellicle frame (support frame) 2 interposed therebetween.

A polarized beam 5 emitted from a laser source 4 enters a scanning lens 11 via a beam splitter 6, a reflecting mirror 8 and a light scanning mirror 9, and the scanning lens 11 condenses the polarized beam 11 on the circuit pattern of the reticle 3. The light scanning mirror 9 can be vibrated or rotated by a driving portion 10, and the scanning lens 11 has a size sufficient to cover the scanning range of the polarized beam 5 by the light scanning mirror. By the light scanning mirror 9 vibrated (or rotated) by the driving portion 10 and the scanning lens 11, the polarized beam 5 can scan the reticle 3 in one direction (X direction). By the reticle 3 being moved in Y direction while the polarized beam 5 is caused to scan, foreign particle inspection becomes possible over the whole surface of the reticle 3. The positional relationship between a light transmission optical system (4, 6, 8, 9, 11) for foreign particle detection and a detecting optical system (13) is fixed and therefore, the angle of incidence of the polarized beam 5 and the angle of emergence of scattered light (the angle formed between the optical axis of the condensing lens of a photoelectric detector 13 leading toward the scanning position of the polarized beam and the normal to the reticle 3) are primarily determined by the light scanning position (x) of the polarized beam 5.

The photoelectric detector 13 has a condensing lens, and receives scattered light from a foreign particle and outputs a signal conforming to the intensity of the scattered light to a correction calculating circuit 12. Two or more photoelectric detectors (13a, 13b) are disposed symmetrically with respect to the center of the light scanning area of the polarized beam on the circuit pattern surface.

The reticle 3 is scanned by the polarized beam through the pellicle film 1, and scattered light created from a foreign particle by the polarized beam being applied to the foreign particle is received by the photoelectric detector 13 through the pellicle film 1, and the magnitude of the detection signal is compared with a predetermined slice level, whereby the foreign particle on the reticle 3 is detected.

The correction calculating circuit 12, prior to the actual foreign particle detection, accumulates the transmittance of the pellicle film 1 for the polarized beam (incident light transmittance) and the transmittance of the pellicle film 1 for a non-polarized beam (hereinafter referred to as the "non-polarized beam transmittance") in a memory for each angle of incidence of the beam (the angle of incidence primarily determined by the scanning position of the polarized beam), and effects the correction calculation of multiplying the detection signal of the scattered light from the photoelectric detector 13 during the actual foreign particle detection by the inverse number of the product value of the incident light transmittance corresponding to the angle of incidence (i.e., corresponding to the scanning position of the polarized beam) and the non-polarized beam transmittance. That is, the correction calculating circuit 12 uses the non-polarized beam transmittance for the transmittance of the pellicle film 1 for the scattered light (uses the non-polarized beam transmittance for the scattered light transmittance) and effects the correction calculation to thereby correct any variation in foreign particle detection sensitivity.

A description will now be given of means for measuring the incident light transmittance and the non-polarized beam transmittance by the use of the actual pellicle film 1. The present embodiment has a transmittance measuring portion discretely from a foreign particle detecting portion, and uses the light source 4 for both of foreign particle detection and transmittance measurement.

A polarized beam 16 emitted from the light source 4 and transmitted through the beam splitter has its polarized state released by an optical fiber bundle 17 and is converted into a non-polarized beam 18. The non-polarized beam 18 becomes a non-polarized beam 23 of a quantity of light permitted to pass through a field stop 19 and an aperture stop 20, and the non-polarized beam 23 passes through a lens 21 to a point M on a rotatable mirror 22. The non-polarized beam 23 reflected by the point M irradiates the pellicle film 1 via a lens 24, a mirror 25 and a lens 26, and in a quantity of light permitted to pass through the aperture stop 20, the shape of the opening in the field stop 19 is projected onto the pellicle film 1. The rotatable mirror 22 is rotatable about the point M by a driving system, not shown, so that the non-polarized beam 23 may be displaced within the angle range of optical paths 28–29, and can vary the angle of incidence of the non-polarized beam 23 onto the pellicle film 1. The center of rotation of the rotatable mirror 22 and the condensing point O of the non-polarized beam 23 are in a conjugate relation with each other, and if the level of the pellicle film 1 is adjusted so that the condensing point O and the pellicle film 1 may coincide with each other, the non-polarized beam 23 will inpinge on the point O on the pellicle film 1 even if the rotatable mirror 22 is rotated. A non-polarized beam 30 (regularly reflected light) reflected by the pellicle film 1 enters a beam splitter 36 via a lens 31, a mirror 32 and a lens 33. The non-polarized beam 30 transmitted through the beam splitter 36 enters a photoelectric converter 35. The photoelectric converter 35 outputs a signal conforming to the light intensity of the received non-polarized beam to a transmittance calculating circuit 14. The non-polarized beam 30 reflected by the beam splitter 36 is converted into a polarized beam by a polarizing plate 37 for extracting the same polarized component as a polarized beam, after which it enters a photoelectric converter 34. The photoelectric converter 34 outputs a signal conforming to the light intensity of the received polarized beam to the transmittance calculating circuit 14. The photoelectric surfaces of the photoelectric converters 34 and 35 are disposed at locations conjugate with the point O on the pellicle film 1. A photoelectric converter 39 detects the intensity of the non-polarized beam 23 and outputs a signal conforming to that intensity to the transmittance calculating circuit 14. The transmittance calculating circuit 14 divides the detection output of the photoelectric detector 34 by the output of the photoelectric converter 39 (divides the intensity of the reflected light by the intensity of the incident light) to thereby find a reflectance, and finds the difference thereof from total reflectance (131 reflectance) to thereby calculate the incident light transmittance. Likewise, the transmittance calculating circuit 14 divides the detection output of the photoelectric detector 35 by the output of the photoelectric converter 39 (divides the intensity of the reflected light by the intensity of the incident light) to thereby find a reflectance, and finds that difference thereof from total reflectance (1−reflectance) to thereby calculate the non-polarized beam transmittance. Here, the absorption by the pellicle film 1 is neglected, and this is because the pellicle film 1 is as thin as the order of 1 μm and the absorption factor of the pellicle film 1 can be neglected in the wavelength range (visible light range) of light generally used as a light source.

In the foreign particle inspecting apparatus thus constructed, the reticle 3 is first carried into a transmittance measuring position (a position at which the non-polarized beam 23 is applied). The rotatable mirror 22 is then rotated so that the non-polarized beam 23 may enter the pellicle film 1 within the range of the angle of incidence varying in conformity with the light scanning position of the polarized beam 5 (detecting light) during the actual foreign particle inspection. In conformity with the rotation of the rotatable mirror 22 (in conformity with the angle of incidence of the non-polarized beam), the intensity of the reflected light 30 is measured by the photoelectric detector 34. Subsequently, the rotatable mirror 22 is rotated so that the non-polarized beam 23 may enter the pellicle film 1 within the range of the angle of emergence of the scattered light from a foreign particle which varies in conformity with the light scanning position of the polarized beam 5 during the actual foreign particle inspection. In conformity with the rotation of the rotatable mirror 22 (in conformity with the angle of incidence of the non-polarized beam), the intensity of the reflected light 30 is measured by the photoelectric detector 35. The rotatable mirror 22 is then rotated to thereby cause all of the non-polarized beam 23 to enter the photoelectric converter 39, and the intensity of the non-polarized beam 23 is measured.

"Incident light transmittance $Ti(\theta)$ conforming to the angle of incidence by scanning" and "non-polarized beam transmittance $Td(\theta)$ conforming to the angle of incidence by scanning" which have been calculated in the transmittance calculating circuit 14 on the basis of the measured value by the photoelectric detector 34, the measured value by the photoelectric detector 35 and the measured value by the photoelectric detector 39 are sent as an output t to the correction calculating circuit 12 and stored in the correction calculating circuit 12 in a callable state correspondingly to a light scanning position (X coordinates value). In other words, they are stored as transmittance data at the angle of incidence and the angle of emergence which are the functions of the light scanning position (X coordinates value) in a callable state correspondingly to the X coordinates value.

Thereafter, the reticle 3 is sent to a foreign particle detecting position, where the detection of any foreign particle on the reticle 3 is effected.

A polarized beam 7 resulting from the incident light 16 onto the optical fiber bundle 17 being excluded from the polarized beam 5 output from the light source 4 is light-scanned on the reticle 3 (on the circuit pattern) in X direciton by the light scanning mirror 9. When the reticle 3 is moved in Y direction and a foreign particle exists on the scanning line 1, scattered light is radiated from the foreign particle irradiated with the polarized beam 7 to the space above it, and only small part of the scattered light travels toward the detecting optical path and enters the photoelectric detector 13. In the correction calculating circuit 12, the applied position of the polarized beam 7 on the reticle 3 is found from the scanning position (x) of the polarized beam 7 put out as an output s from the driving portion 10 and Y coordinates value put out from a Y direction feeding mechanism, and the incident light transmittance $Ti(\theta)$ and non-polarized beam transmittance $Td(\theta)$ corresponding thereto are called out to thereby correct the output signal of the photoelectric detector 13.

In the foreign particle inspecting apparatus of FIG. 1, as long as foreign particle detection is effected on the reticle 3, the next reticle is set at the transmittance measuring position (the right-hand side of FIG. 1) and the measurement of the incident light transmittance $Ti(\theta)$ and non-polarized beam transmittance $Td(\theta)$ by the actual pellicle film to be subsequently subjected to foreign particle inspection is effected. Also, the non-polarized beam 18 is caused to enter the photoelectric detector 39 to thereby measure the intensity of the non-polarized beam 23 (reflected light 30) entering the pellicle film 1 and therefore, reflectance (finally transmittance) can be measured accurately even when the output of the light source 4 varies with the lapse of time.

Figure 2B:
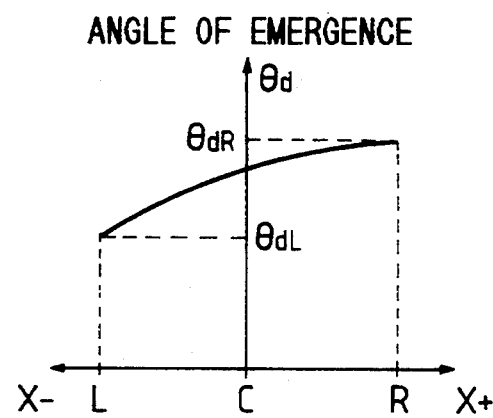
FIG. 2B shows the relation of the angle of emergence of scattered light to the position of incidence of the polarized beam in the apparatus of FIG. 1.

FIG. 2A shows the variation in the angle of incidence of the polarized beam by the light scanning of the polarized beam 7, and FIG. 2B shows the variation in the angle of emergence of the scattered light by the light scanning of the polarized beam 7. The polarized beam 7 of FIG. 1 is light-scanning in X direction (a direction perpendicular to the plane of the drawing sheet of FIG. 1) with this side (L) as − (minus) and that side (R) as + (plus) with the center X of the light scanning area as the origin, and in conformity with the light scanning position X from the scanning position L to the scanning position R, the angle of incidence of the polarized beam 7 varies to $\theta_{il}-\theta_{ic}-\theta_{iR}$, while the angle of emergence of the scattered light varies to $\theta_{dl}-\theta_{dc}-\theta_{dR}$.

Figure 3:
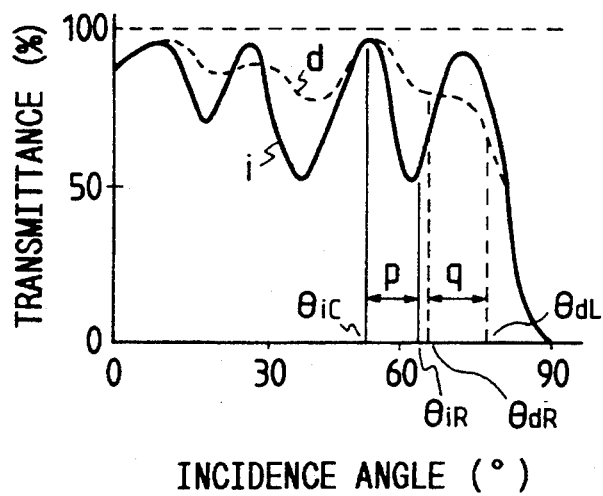
FIG. 3 is a graph showing the transmittance characteristic of the pellicle of FIG. 1.

In FIG. 3, in the foreign particle inspecting apparatus and reticle of FIG. 1, the thickness (about 1 μm) of the pellicle film 1 is of the same order as the wavelength 0.6 μm of the polarized beam 7, and since the polarized beam 7 is monochromatic light, the wavelength selectivity by the pellicle film 1 is added and the transmittance $Ti(\theta)$ of the pellicle film 1 for the polarized beam 7 varies greatly in conformity with the angle of incidence. However, the variation in the transmittance of the pellicle film 1 for the scattered light from the foreign substance which conforms to the angle of incidence (the angle of emergence) is approximate to the variation in the non-polarized beam transmittance $Td(\theta)$, and the former transmittance varies more gently in conformity with the angle of incidence than the transmittance $Ti(\theta)$. Accordingly, in the method described in the foreign particle inspecting apparatus of U.S. Pat. No. 4,889,998, incident light transmittance is used for scattered light transmittance and therefore, there arises an error corresponding to the difference between the transmittance d for the non-polarized beam and the transmittance i for the polarized beam 7. Also, in the graph of FIG. 3, in the foreign particle inspecting apparatus (the transmittance measuring portion) of FIG. 1, the range p in which the transmittance i for the polarized beam is actually measured is only a range corresponding to $\theta_{il}-\theta_{ic}-\theta_{iR}$ of FIG. 2A, and the range q in which the transmittance d for the non-polarized beam is measrued is only a range corresponding to $\theta_{dl}-\theta_{dc}-\theta_{dR}$ of FIG. 2B.

Figure 4:
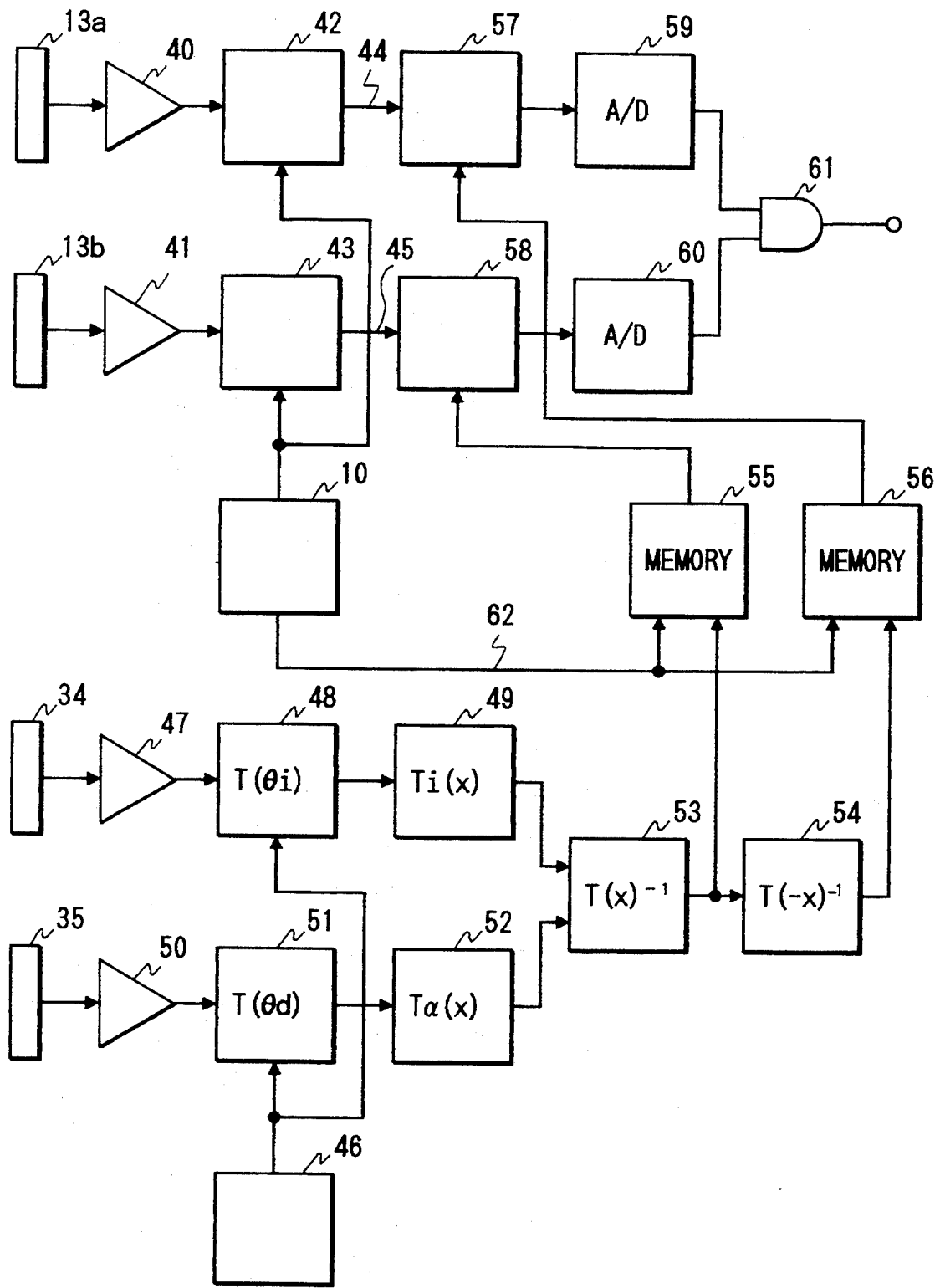
FIG. 4 is a circuit diagram of a correction calculating circuit and a transmittance calculating circuit in the foreign particle inspecting apparatus of FIG. 1.

FIG. 4 is a block diagram showing the signal processing circuit of the apparatus of FIG. 1. In FIG. 4, the output signals of photoelectric detectors 13a and 13b are amplified by amplifiers (preamplifiers) 40 and 41, respectively, and are input to variable amplifiers 42 and 43, respectively. In the variable amplifiers 42 and 43, amplification degree is varied in conformity with the scanning angle output from the driving portion 10 for the scanning mirror 9, i.e., the scanning position in X direction. This is for correcting the foreign particle signal at a position farther from the photoelectric detector becoming greater in the amount of signal than the foreign particle signal at a position nearer to thee photoelectric converter even when the pellicle film 1 is absent. For example, to the photoelectric detector 13a located at that side of the reticle 3, the point R at that side on the scanning line 1 is shorter in its distance from the photoelectric detector 13a than the point L at this side on the scanning line 1, and the foreign particle signal received by the photoelectric detector becomes greater and therefore, the design is such that the amplification factor is made smaller toward the point R at that side and equal foreign particle signals are obtained in whatever position on the scanning line 1. In this manner, signals 44 and 45 output from the variable amplifiers 42 and 43, respectively, provide the signals immediately before the reduction in quantity of light by the transmittance of the pellicle film is corrected.

The determination of the pellicle film transmittance correction value at the right-hand transmittance actual measuring position in FIG. 1 is effected prior to the actual foreign particle inspection. At this time, the rotatable mirror 22 is rotated by the driving portion 46 therefor. The non-polarized beam is reflected by the pellicle film and the light split by the beam splitter 36 becomes polarized light through the polarizing element 37, and the polarized light is photoelectrically converted by the photoelectric detector 34. If the quantity of light of the polarized beam output from the laser source 4 is always constant, reflectance will be obtained simply by multiplying the electrical signal obtained from the photoelectric detector 34 by a count number. This count number is determined with the amplification degree of the amplifier 47 taken into account. When the rotatable mirror 22 is driven by the driving portion 46 so that $\theta_i$ may vary within the range of $\theta_{iL}$ to $\theta_{iR}$, reflectance $Ri(\theta i)$ is obtained between $\theta_{iL}$ and $\theta_{iR}$, but since the absorption of the laser beam by the pellicle film is null, the incident light transmittance $Ti(\theta i)$ is found from $Ti(\theta i) = 1 - Ri(\theta i)$.

This process is carried out in a calculating portion 48. Also, as shown in FIG. 2A, the relation between the x position on the scanning line 1 and the angle of incidence $\theta i$ is determined in the apparatus and therefore, when the scanning position coordinates X are converted into the angle of incidence $\theta i$ by a converting portion 49, the incident light transmittance $Ti(\theta i)$ conforming to the X coordinates position is found. Also, information (electrical signal) regarding the pellicle reflectance (exactly, reflected light) of the non-polarized beam is output from the photoelectric detector 35, and reflectance $Rd(\theta d)$ is obtained by an amplifier 50. As when the incident light transmittance $Ti(\theta i)$ has been found, the rotatable mirror 22 is driven by the driving portion 46 so that $\theta d$ may vary within the range of $\theta_{dL}$ to $\theta_{dR}$. The non-polarized beam transmittance (received light transmittance) $Td(\theta d) = 1 - Rd(\theta d)$ is calculated by a calculating portion 51, whereby the non-polarized beam transmittance $Td(\theta d)$ is calculated. Further, the non-polarized beam transmittance $Td(\theta d)$ conforming to the X coordinates position is found by a converting portion 52 on the basis of the relation between the x position on the scanning line 1 and the angle of incidence $\theta d$ shown in FIG. 2B. A multiplier 53 finds a value $T(x) = Ti(\theta i) \times Td(\theta d)$ obtained by multiplying the incident light transmittance $Ti(\theta i)$ obtained by the converting portion 49, by the non-polarized beam transmittance $Td(\theta d)$ obtained by the converting portion 52, and further a value $T(x)^{-1}$ (the inverse number of a value $T(x)$) for detection sensitivity correction is calculated.

In FIG. 1, the photoelectric detectors 13a and 13b are disposed symmetrically with each other (see FIG. 6), and if the detection sensitivity correction value rate is $T(x)^{-1}$ when viewed from the photoelectric detector 13a, the detection sensitivity correction value rate in the photoelectric detector 13b may of course be the inverse of the sign of x, i.e., $T(-x)^{-1}$. This calculation is effected in a calculating portion 54. The above-mentioned two data, i.e., $T(x)^{-1}$ and $T(-x)^{-1}$, are stored in memories 55 and 56, respectively.

Now, turning back to the description of the foreign particle signal processing, the correction data $T(x)^{-1}$ and $T(-x)^{-1}$ are successively output from the memories 55 and 56 in conformity with the output signal 57 of the light scanning position (x) of the light scanning driving portion 10, and are multiplied by the foreign particle signals 44 and 45 before the correction of the pellicle transmittance in multipliers 57 and 58. The signals thus obtained are converted into digital signals by A/D converters (analog/digital converters) 59 and 60, respectively, and will be detected as foreign particles by an AND circuit 61 if both of the two signals are above a predetermined slice level. This is to discriminate between the circuit pattern and a foreign particle by the utilization of the nature that the directionality of diffracted light from the circuit pattern is strong and the diffracted light does not enter the two photoelectric detectors 13a and 13b at the same time.

The above-described incident light transmittance $Ti(\theta i)$ and non-polarized beam transmittance $Td(\theta d)$ are set for each scanning position on the surface to be inspected and are used for the correction calculation of the detection signal of the scattered light. The inputting of these numerical values may be done by manually setting numerical values theoretically calculated on the basis of the range of the angle of incidence of the polarized beam, the range of the angle of emergence of the scattered light, the thickness of the light transmitting member (pellicle), the wavelength of the polarized beam, etc., correspondingly to each point of intersection in the matrix of the X—Y coordinates of the surface to be inspected.

Also, the incident light transmittance $Ti(\theta i)$ and non-polarized beam transmittance $Td(\theta d)$ are in a predetermined relation conforming to the thickness of the light transmitting member (pellicle) and therefore, only one of the incident light transmittance $Ti(\theta i)$ and the non-polarized beam transmittance $Td(\theta d)$ may be actually measured and the other may be found from this actually measured value by calculation or cross-reference.

A second embodiment of the present invention will now be described.

Figure 5:
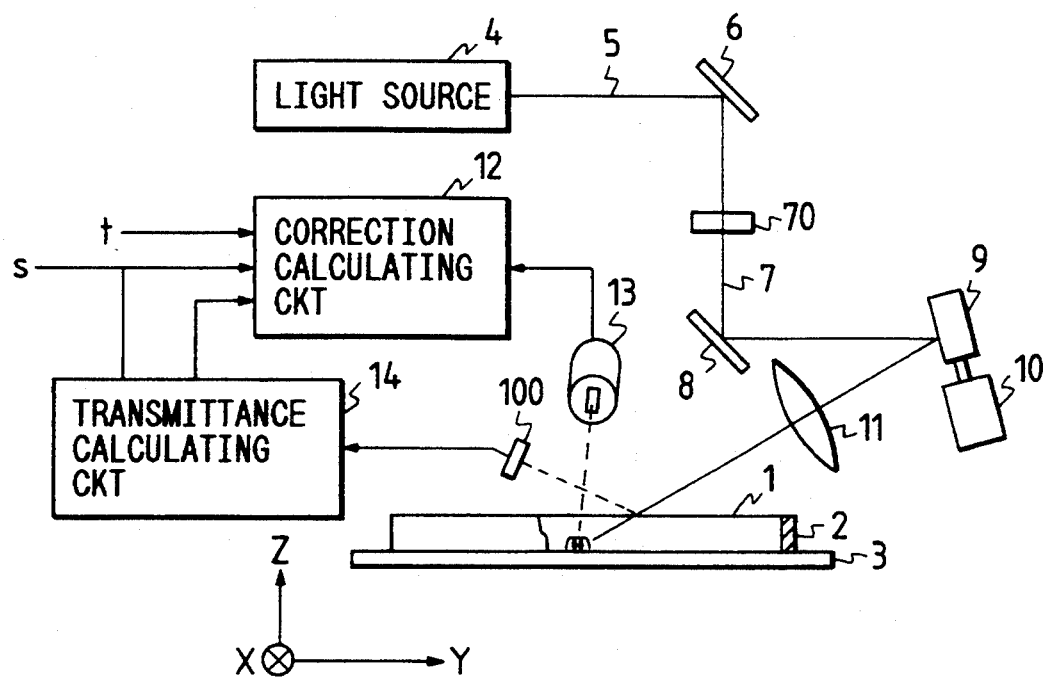
FIG. 5 is a schematic view of a foreign particle inspecting apparatus according to a second embodiment of the present invention.
Figure 6:
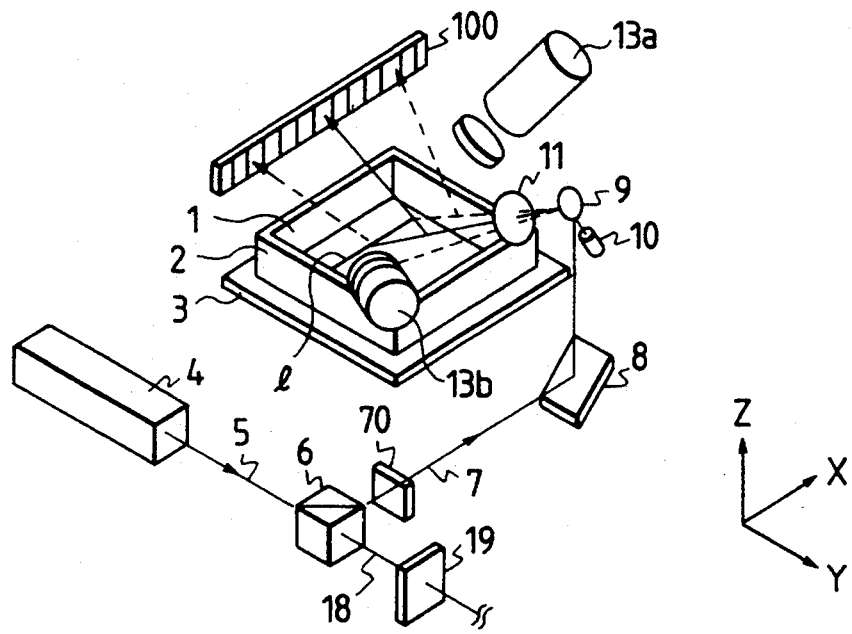
FIG. 6 is a perspective view of the optical system of the apparatus of FIG. 5.

FIG. 5 is a schematic view of a foreign particle inspecting apparatus according to the second embodiment of the present invention, and FIG. 6 is a perspective view of the optical system of the foreign particle inspecting apparatus of FIG. 5. In this embodiment, the pellicle film transmittance for the polarized beam is measured by the use of a foreign particle detecting system, that is, a light transmission optical system (4, 5, 6, 9, 10, 11) for effecting foreign particle detection is utilized as a light transmission optical system for effecting the measurement of the incident light transmittance, and provision is made of a photoelectric detector 100 for measuring thee pellicle transmittance. The non-polarized beam transmittance is measured by the transmittance measuring portion as in the first embodiment.

In FIGS. 5 and 6, the basic light transmission optical system for foreign particle detection is similar to that in the first embodiment, but in the present embodiment, it uses a non-polarized beam. The foreign particle inspecting apparatus according to the present embodiment includes a light source 4 outputting a non-polarized beam, a beam splitter 6, a polarizing plate 70 for converting the non-polarized beam into a polarized beam, a reflecting mirror 8, a scanning mirror 9 adapted to be vibrated by a driving portion 10, a scanning lens 11, etc. A detecting optical system for foreign particle detection includes a photoelectric detector 13 for detecting scattered light from a foreign particle, etc. Further, in the present embodiment, there is provided a photoelectric detector 100 for measuring the incident light transmittance by the polarized beam. The photoelectric detector 100 comprises a plurality of photoelectric detectors arranged at intervals.

A correction calculating circuit 12, as in the first embodiment, prior to the actual foreign particle detection, accumulates the incident light transmittance $Ti(\theta)$ and the non-polarized beam transmittance $Td(\theta)$ for each scanning position (X position) of the polarized beam on the basis of the relation between respective angles and the scanning position. As in the first embodiment, it finds the detection sensitivity correction value $T(x)^{-1}$, and effects the correction calculation of multiplying the output from the photoelectric detector 13 by the detection sensitivity correction value $T(x)^{-1}$ which it is desired to call out at the scanning position (X position) of the polarized beam.

In the foreign particle inspecting apparatus thus constructed, when a reticle 3 is carried to a position at which foreign particle detection is started, the polarized beam is scanned on the pellicle film 1 through the polarizing plate 70, and the intensities of regularly reflected light at angles of incidence corresponding to the desultory values of the light scanning position x are measured by the photoelectric detector array 100. The incident light transmittance calculated by a transmittance calculating circuit 14 on the basis of these intensities of the reflected light is memorized in the correction calculating circuit 12 in conformity with the scanning position (X position).

The sampling resolving power into a memory which conforms to the scanning position (X position) is effected to such a degree that will not adversely affect accuracy, but when the sampling resolving power is rough, there is a case where there are no data corresponding to the scanning position X. In such case, the incident light transmittance at the scanning position X which does not correspond to the desultory values of the actually measured scanning position X of the actually measured apparatus position can be analogically calculated and stored on the basis of the actually measured values of the opposite sides. The analogical calculation is effected by interpolation or by a method of effecting minimum square approximation by a high order equation such as a quaternary equation. This interpolation is equally applicable to the first embodiment.

Thereafter, the actual foreign particle detection is effected in the same manner as in the first embodiment by the polarized beam passed through the polarizing plate 70 being scanned by the light scanning mirror 9, and the correction calculating circuit 12 uses both of the incident light transmittance $Ti(\theta)$ and the non-polarized beam transmittance $Td(\theta)$ accumulated therein to correct the detection signal from the photoelectric detector 13.

Now, in FIG. 6, the apparatus construction from a field stop 19 and so on, although partly simplified, is substantially similar to the apparatus construction from the field stop 19 and so on in FIG. 1. The length of the photoelectric detector 100 in X direction is great so as to be able to receive all of the reflected light from the pellicle even when light scanning is being effected. In this case, the construction of the field stop 19 and so on of FIG. 6 becomes simple as compared with the construction of FIG. 1, because the non-polarized beam is used and therefore the optical fiber is unnecessary and the photoelectric detector 100 measures the incident light transmittance. Thus, the photoelectric detector 34, polarizing element (analyzer) 37 and beam splitter 36 of FIG. 1 become unnecessary, whereby not only the quantity of light entering the photoelectric detector 35 is increased and S/N is improved, but also it becomes unnecessary for the rotatable mirror 22 to be designed such that the angle of incidence $\theta$ is within the range of $\theta_{iL} - \theta_{iR}$. Also, by a similar operation being repeated with the polarizing plate 70 retracted from the optical path to cause the non-polarized beam to enter the pellicle, the non-polarized beam transmittance can also be found in the apparatus of FIGS. 5 and 6. In the present embodiment, use may be made of a light source 4 emitting a polarized beam and the measurement of the incident light transmittance may be effected by the use of the photoelectric detector 100. In such case, polarized state releasing means such as optical fiber 17 will become necessary.

As a common application of the above-described first and second embodiments, the polarized laser (or a combination of a laser and a polarizing element) for foreign particle inspection and the laser for pellicle measurement may be made discrete from each other. For example, a linearly polarized He—Ne laser may be used for foreign particle inspection and a random polarized He-Ne laser may be used for transmittance measurement, and the pellicle transmittance may be measured with the beam divided into a random (non-polarized) component and a polarized component.

Further, the present invention does not restrict the angle of incidence of light in the foreign particle inspecting apparatus, the angle of light reception of the light receiving device, the light scanning of the incident light, etc., but is also applied to a method of inspecting any foreign particle on a reticle through pellicle film as a fall light field and fall dark field illuminating method and a transmission illuminating method. The present invention can also be applied to apparatuses for inspecting any defect such as a foreign particle through a light transmitting substrate instead of through a pellicle.

A third embodiment of the present invention will now be described. The third embodiment uses a reference pellicle and a reference particle to find incident light transmittance and scattered light transmittance.

Figure 7:
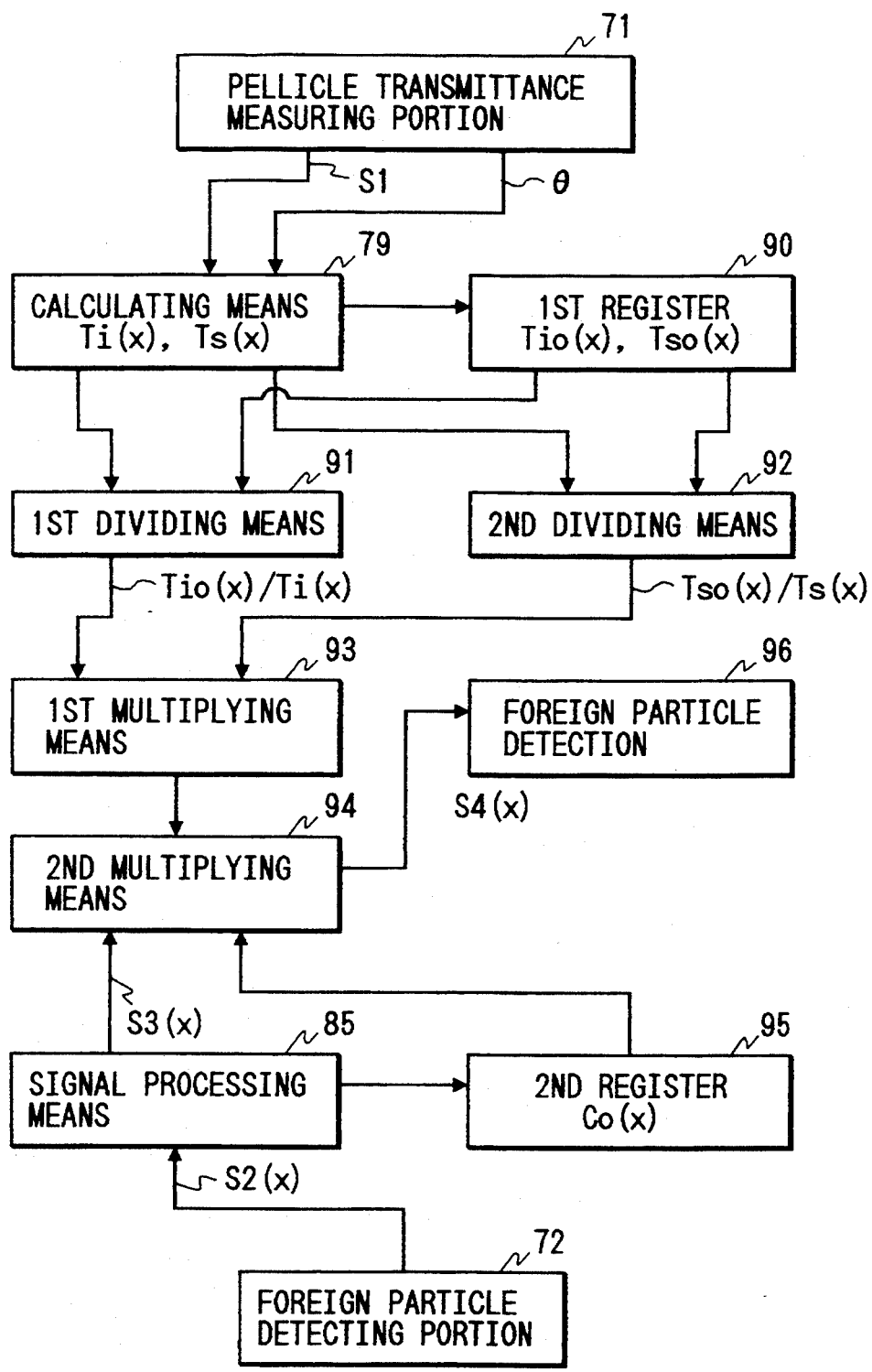
FIG. 7 is a block diagram showing the system construction of a foreign particle inspecting apparatus according to a third embodiment of the present invention.
Figure 8:
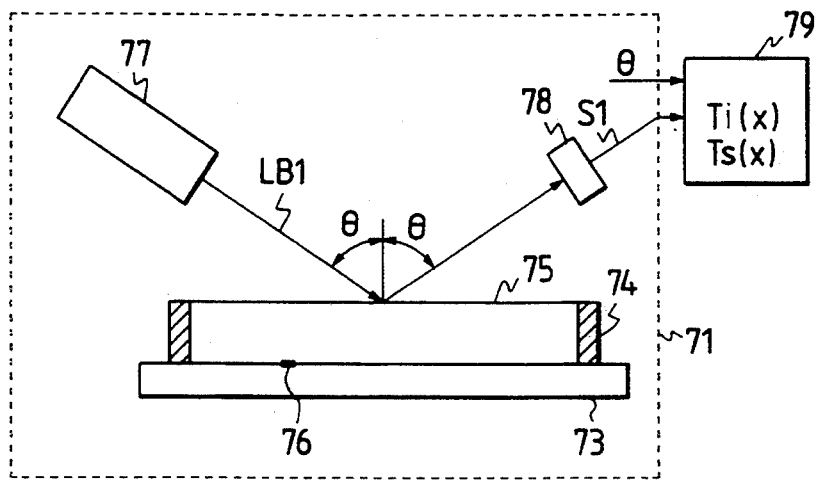
FIG. 8 illustrates the pellicle measuring portion of FIG. 7.

FIG. 7 shows the system construction of a foreign particle inspecting apparatus according to the present embodiment. FIG. 8 shows the construction of the pellicle transmittance measuring portion 71 of FIG. 7. In FIG. 8, a pellicle 75 is extended on the pattern forming surface of a reticle 73 with a support frame (pellicle frame) 74 interposed therebetween. A foreign particle 76 to be detected adheres to that surface of the reticle 73 which is inside the pellicle 75. A laser beam LB1 emitted from a laser source 77 which produces a laser beam of the same wavelength as a laser beam used in a foreign particle inspecting portion 72 which will be described later is incident on the pellicle 75 at an angle of incidence $\theta$, and a laser beam reflected on the pellicle 75 at an angle of reflection $\theta$ enters a light receiving element 78. A detection signal S1 obtained by the laser beam being photoelectrically converted by this light receiving element 78 is supplied to calculating means 79.

In this case, the relative positional relationship between the laser source 77 and the light receiving element 78 is set by an angle adjusting mechanism, not shown, so that the angle of incidence $\theta$ of the laser beam LB1 from the laser source 77 and the angle $\theta$ formed by a straight line extending from the center of the light receiving element 78 toward the point of incidence of the laser beam LB1 on the pellicle 75 with respect to a straight line perpendicular to the pellicle 75 (hereinafter referred to as the "angle of light reception $\theta$") may always coincide with each other. When it is desired to measure the transmittance characteristic of the pellicle 75 at a plurality of angles of incidence, the reflected light from the pellicle 75 can be detected with the angle of incidence $\theta$ of the laser beam LB1 from the laser source 77 and the angle of light reception $\theta$ of the light receiving element 78 changed by the angle adjusting mechanism. The information of the then angle of incidence $\theta$ is also supplied to the calculating means 79.

In the calculating means 79, the transmittance of the pellicle 75 is calculated in the following manner. Since the detection signal S1 output from the light receiving element 78 is a signal proportional to the intensity of the reflected light from the pellicle 75, the intensity of the light transmitted through the pellicle 75 can be calculated by comparing the detection signal S1 when the laser beam LB1 emitted from the laser source 77 is directly received with the detection signal S1. Specifically, the laser beam LB1 is directly received in advance by the light receiving element 78 and the then value of the detection signal S1 is memorized. When a detection signal obtained by the laser beam reflected from the pellicle 75 at the angle of reflection $\theta$ being received by the light receiving element 78 is Sr, the intensity St of the light transmitted through the pellicle 75 can be calculated from the following equation using a predetermined coefficient K:

$$St = K(Si - Sr)$$

Also, the transmittance T of the pellicle 75 for the laser beam LB1 is calculated as follows:

$$T = St/(K \cdot Si) = (Si - Sr)/Si$$

Here, the light absorption of the pellicle 75 is neglected, but generally the thickness of the pellicle 75 is as small as 1 $\mu$m and therefore, the light absorption thereof is sufficiently negligibly small. Also, the wavelength of the laser beam LB1 used in this embodiment is the same as that of the laser beam used in the foreign particle inspecting portion 72 which will be described later, but the transmittance of the pellicle 75 can be estimated substantially accurately even if a different wavelength is used.

Also, when the detection of the foreign particle 76 on the reticle 73 is to be effected, the laser beam is transmitted twice through the pellicle 75, i.e., when the foreign particle 76 is irradiated and when the light is scattered from the foreign particle 76. Accordingly, it is necessary to measure the transmittance Ti at an angle of incidence $\theta 1$ onto the pellicle 75 when the laser beam irradiates the foreign particle 76 and the transmittance Ts of the pellicle 75 at the angle of incidence $\theta 2$ of the laser beam scattered from the foreign particle 76 onto the pellicle 75 (which angle corresponds to the angle of emergence in the first and second embodiments). In this case, in the pellicle transmittance measuring portion 71, a laser beam is applied onto the reticle 73 through the pellicle 75 and this laser beam is scanned in a predetermined direction (which is defined as "X direction"). The angle of incidence $\theta 1$ of the laser beam onto the pellicle 75 and the angle of incidence $\theta 2$ onto the pellicle 75 are the functions of the respective coordinates x thereof in X direction.

Accordingly, the transmittance Ti at the angle of incidence $\theta 1$ of the incident laser beam can be represented by Ti(x) as the function of the coordinates x, and the transmittance Ts at the angle of incidence $\theta 2$ of the scattered beam can be represented by Ts(x) as the function of the coordinates x. The calculating means 79 calculates the transmittance Ti(x) of the laser beam incident on the pellicle 75 and the transmittance Ts(x) of the scattered beam transmitted through the pellicle 75, correspondingly to the coordinates x of the scanning position on the reticle 73.

Figure 9:
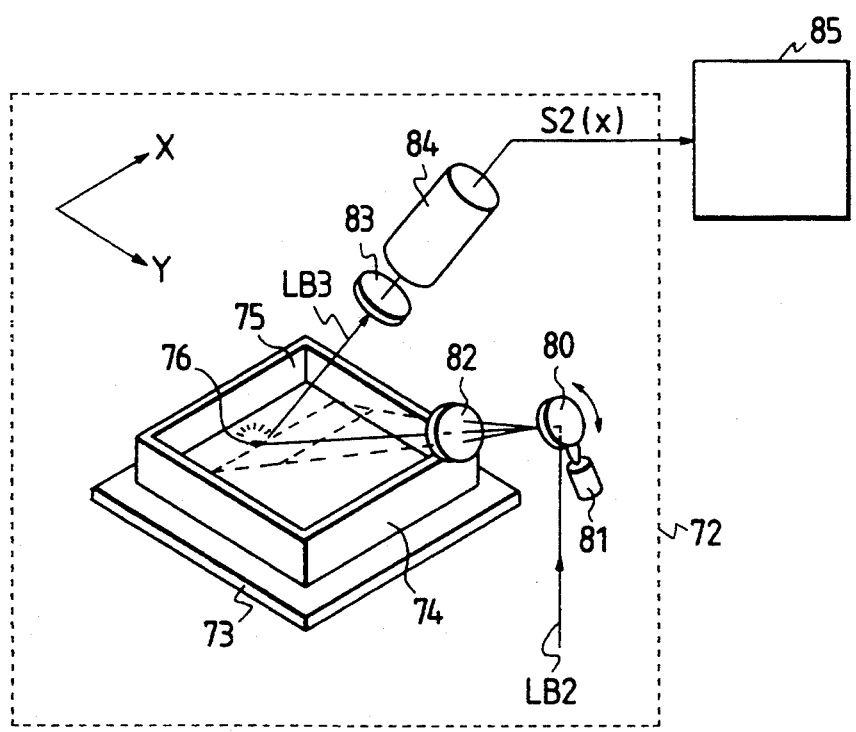
FIG. 9 is a perspective view showing the foreign particle inspecting portion of FIG. 7.

FIG. 9 shows the construction of the foreign particle inspecting portion 72 of FIG. 7. Basically, this foreign particle inspecting portion 72 is of the same construction as the foreign particle inspecting portion of FIG. 1. In FIG. 9, the pellicle 75 is extended on the pattern area of the reticle 73 to be inspected with the support frame 74 interposed therebetween. A laser beam LB2 emitted from a laser source, not shown, impinges on a galvano mirror 80, and the laser beam LB2 reflected by this galvano mirror 80 is transmitted through the pellicle 75 with the aid of a scanning lens 82 and is applied onto the reticle 73. By the galvano mirror 80 being vibrated by a scanner 81, that laser beam scans the reticle 73 in X direction. Also, by the use of a driving mechanism, not shown, the reticle 73 is moved in Y direction perpendicular to X direction, whereby the laser beam two-dimensionally scanners the reticle 73.

If a foreign particle 76 exists on the reticle 73, scattered light LB3 is created from the foreign particle 76 and this scattered light LB3 enters the light receiving surface of a photoelectric detector 84 through a condensing lens 83. A detection signal S2(x) obtained by the scattered light LB3 from the foreign particle on the coordinates x in X direction being photoelectrically converted by the photoelectric detector 84 is supplied to signal processing means 85. The intensity of the scattered light detected by the photoelectric detector 84 varies in conformity with the scanning position x in which the laser beam LB2 scans the reticle 73 and therefore, in the signal processing means 85, there is adapted a means for making uniform the variation in detection sensitivity caused by the adhering location of the foreign particle, by a method as proposed, for example, in U.S. Pat. No. 4,468,120.

Now, where the pellicle 75 is extended above the reticle 73, the laser beam LB2 is generally incident obliquely on the pellicle 75 and therefore, the transmittance of the pellicle 75 is not 1. Further, where an incident beam optical system (the scanning lens 82, etc.) is not telecentric, the angle of incidence of the laser beam is varied by the scanning position x of the laser beam and the transmittance does not become constant.

With regard also to the scattered light from the foreign particle on the reticle 73 which enters a light receiving optical system (the condensing lens 83, etc.), the angle formed between the ray of the scattered light and the pellicle 75 is varied by the scanning position and therefore, the transmittance does not become constant. Therefore, it is necessary to feed back the transmittance characteristic of the pellicle 75 in advance to thereby correct the detection signal S2(x), etc. as will be described later.

In the present embodiment, there is adopted a method of actually measuring the transmittance characteristic of the pellicle 75 before the inspection of the foreign particle on the reticle 73. The transmittance characteristic of the pellicle 75 is measured by a simple pellicle transmittance measuring portion 71 shown in FIG. 8. However, this pellicle transmittance measuring portion 71 differs in system from the foreign particle inspecting portion 72 from which is output the detection signal S2(x) for actually effecting the correction of the transmittance and therefore, if the correction of the detection signal S2(x) is effected at the percentage of the transmittance of the pellicle 75 for a case where the transmittance is 1, that is, the pellicle is absent, accurate correction cannot be accomplished.

Figure 10:
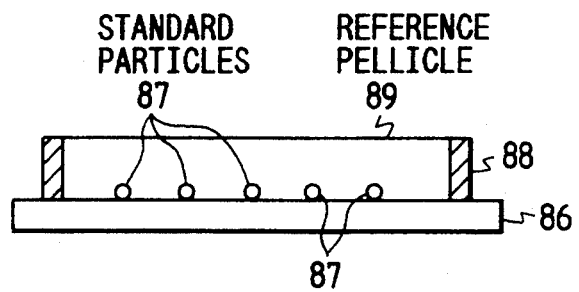
FIG. 10 shows a reference object to be inspected comprising a reticle having a reference pellicle mounted thereon.

So, in the present embodiment, use is made of a reference object to be inspected having a reference pellicle 89 mounted on a reticle 86 having attached thereto standard particles 87 for foreign particle inspection sensitivity correction as shown in FIG. 10, with support frame 88 interposed therebetween, whereby the above-noted problem is solved as follows. The method will now be described with the system construction of FIG. 7.

In FIG. 7, when the transmittance of the reference pellicle 89 of FIG. 10 of the reference object to be inspected is measured by the pellicle transmittance measuring portion 71, the transmittance $T_{i0}(x)$ of the reference pellicle 89 for the incident beam and the transmittance $T_{s0}(x)$ of the reference pellicle 89 for the scattered beam which are calculated by calculating means 79 are stored in a first register 90. Thereafter, when the transmittance of the pellicle 75 of FIG. 8 to be inspected is measured by the pellicle transmittance measuring portion 71, the transmittance Ti(x) of the pellicle 75 for the incident beam and the transmittance Ts(x) of the pellicle 75 for the scattered beam which are calculated by the calculating means 79 are supplied to first dividing means 91 and second dividing means 92, respectively, and the transmittance $T_{i0}(x)$ and transmittance $T_{s0}(x)$ stored in the first register 90 are supplied to the first dividing means 91 and the second dividing means 92, respectively. The first dividing means 91 calculates the ratio $T_{i0}(x)/Ti(x)$ of the two transmittances and supplies it to one input portion of first multiplying means 93, and the second dividing means 92 calculates the ratio $T_{s0}(x)/Ts(x)$ of the two transmittances and supplies it to the other input portion of the first multiplying means 93. This first multiplying means 93 supplies a first input portion of second multiplying means 93 with a value obtained by multiplying the supplied two ratios.

On the other hand, a detection signal $S2_0(x)$ output from the photoelectric detector 84 when the scattered light from the standard particles 87 of FIG. 10 on the reference object to be inspected is detected by the foreign particle inspecting portion 72 is supplied to signal processing means 85, in which is obtained a foreign particle detection signal $S3_0(x)$ before correction provided from the detection signal $S2_0(x)$ except a DC signal or the like. Also, when a standard foreign particle detection signal obtained for the standard particles 87 (a standard signal which should be obtained for the standard particles 87) is SS, the signal processing means 85 finds a pellicle sensitivity correction value $C_0(x)$ by the following calculation:

$$C_0(x)=SS/S3_0(x)$$

When this pellicle sensitivity correction value $C_0(x)$ is multiplied by the foreign particle detection signal $S3_0(x)$, there is obtained the standard foreign particle detection signal SS. The pellicle sensitivity correciton value $C_0(x)$ is stored in a second register 95. Subsequently, a detection signal S2(x) output from the photoelectric detector 84 when the scattered light from a foreign particle on the reticle 73 of FIG. 9 to be inspected is detected by the foreign particle inspecting portion 72 is supplied to the signal processing means 85, in which a foreign particle detection signal S3(x) before correction obtained from the detection signal S2(x) except a DC signal or the like is supplied to a second input portion of the second multiplying means 94 of FIG. 7, and the pellicle sensitivity correction value $C_0(x)$ stored in the second register 95 is supplied to a third input portion of the second multiplying means 94.

In the second multiplying means 94, there is produced a foreign particle detection signal S4(x) in which the transmittance has been corrected by the following calculation:

$$S4(x)=S3(x)\cdot C_0(x)\cdot T_{i0}(x)\cdot T_{s0}(x)/[Ti(x)\cdot Ts(x)] \qquad (1)$$

This foreign particle detection signal S4(x) is a signal in which the influence of the transmittance of the pellicle 75 has been corrected for the foreign particle detection signal S3(x) , and the foreign particle detecting means 96 of FIG. 7 processes the foreign particle detection signal S4(x) and effects the detection of any foreign particle.

An example of the general operation when the detection of any foreign particle on the reticle 73 to be inspected shown in FIG. 8 is effected by the use of the reference object to be inspected shown in FIG. 10 will now be described with reference to FIG. 11.

Figure 11:
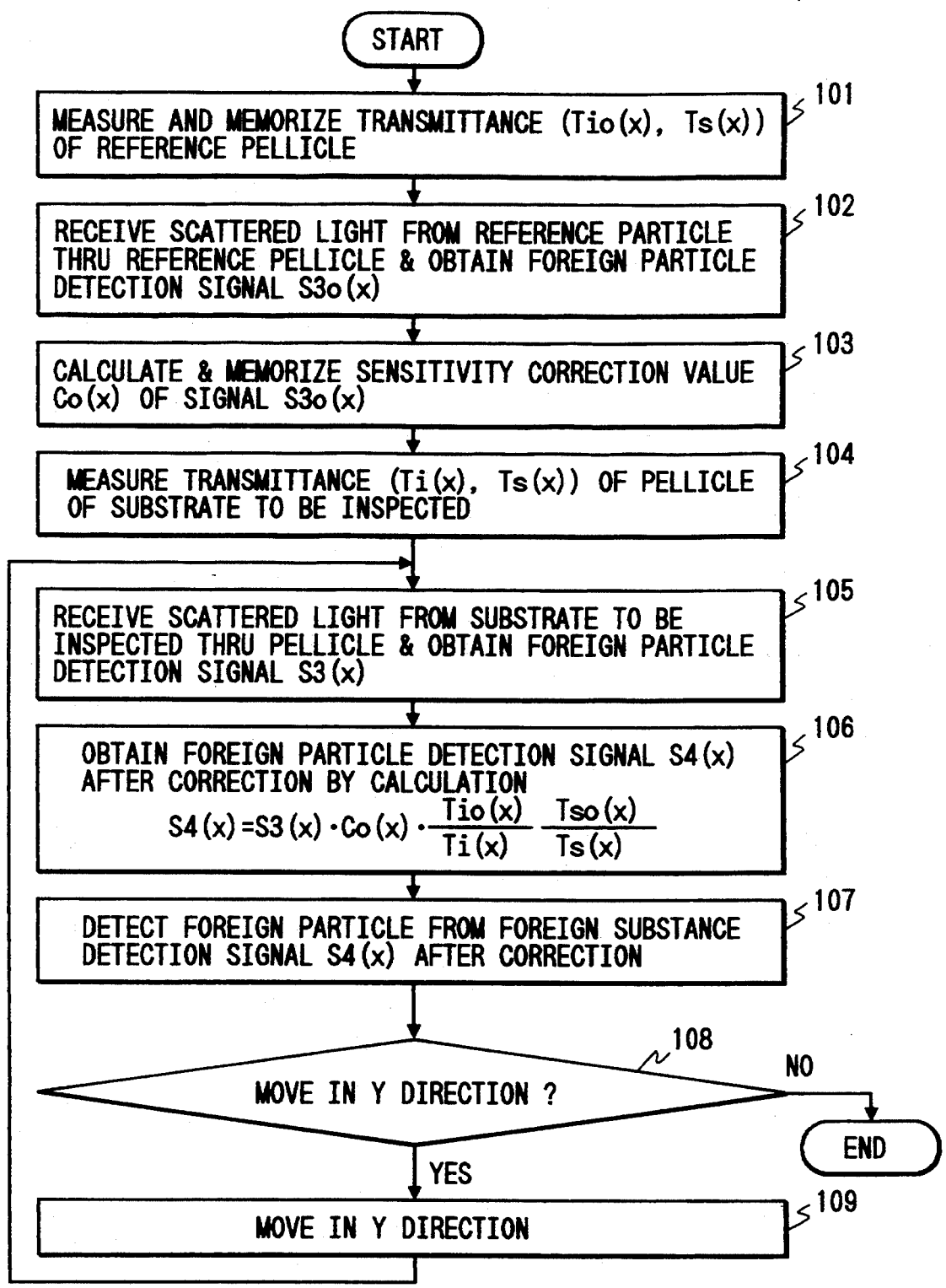
FIG. 11 is a flow chart showing an example of the foreign particle detecting operation by the third embodiment of the present invention.

First, at the step 101 of FIG. 11, the pellicle transmittance measuring portion 71 and the calculating means 79 measure the transmittance $T_{i0}(x)$ of the reference pellicle 89 of the reference object to be inspected of FIG. 10 for the incident beam and the transmittance $T_{s0}(x)$ of the reference pellicle 89 for the scattered light and causes these transmittances to be stored in the first register 90. The coordinates x are the coordinates of the scanning position of the laser beam on the reticle 86. Subsequently, at a step 102, the standard particles 87 on the reticle 86 having mounted thereon the reference pellicle 89 whose transmittance characteristic has been measured are detected by the foreign particle inspecting portion 72. At this time, as previously described, the intensity of the scattered signal from the standard particles 87 is attenuated by the reference pellicle 89 and therefore, the detection signal $S2_0(x)$ supplied to the signal processing means 85 becomes smaller than the detection signal when the pellicle is absent. A foreign particle detection signal $S3_0(x)$ is obtained from the detection signal $S2_0(x)$.

In order to keep detection sensitivity constant even if the pellicle is present, it is necessary to apply a correction to the foreign particle detection signal by an amount corresponding to the inverse number of the amount of reduction in sensitivity by the pellicle. This correction value is used as the pellicle sensitivity correction value, and at a step 103, a pellicle sensitivity correction value $C_0(x)$ for the reference pellicle 89 (hereinafter referred to as the "reference pellicle sensitivity correction value") is found from the result of said detection and is stored as an initial value in the second register 95. The coordinates x are the same x as the aforementioned coordinates indicating the scanning position.

Subsequently, at a step 104, the transmittances $Ti(x)$ and $Ts(x)$ of the pellicle 75 mounted on the reticle 73 of FIG. 8 to be inspected are measured by the pellicle transmittance measuring portion 71 and the calculating means 79. Thereafter, at a step 105, the reticle 73 to be inspected is set in the foreign particle inspecting portion 72 and the scattered light from the reticle 73 is received through the pellicle 75. A foreign particle detection signal $S3(x)$ before correction is then obtained from the signal processing means 85. At a step 106, a foreign particle detection signal $S4(x)$ after correction is obtained by the calculation of equation (1) above, whereafter at a step 107, the foreign particle detection processing means 96 effects foreign particle detection from the foreign particle detection signal $S4(x)$.

The ratio of the transmittance characteristic of the pellicle 75 to the transmittance characteristic of the reference pellicle 89, i.e., the amount of variation in sensitivity, is calculated by the calculation of $[T_{i0}(x)/Ti(x)] \cdot [T_{s0}(x)/Ts(x)]$ in the calculation of equation (1). By multiplying this amount of variation in sensitivity by the reference pellicle sensitivity correction value $C_0(x)$, there is found a sensitivity correction coefficient necessary for the pellicle 75 in the foreign particle inspecting portion 72. Accordingly, by multiplying the foreign particle detection signal $S3(x)$ for the foreign particle on the reticle 73 having the pellicle 75 mounted thereon by the sensitivity correction coefficient, there can be obtained a foreign particle detection signal $S4(x)$ in which the influence of the transmittance of the pellicle 75 has been accurately corrected.

Subsequently, at the step 108 of FIG. 11, whether the reticle 73 should be moved in Y direction in FIG. 3 is examined, and when it should be moved in Y direction, at a step 109, it is moved in Y direction, whereafter shift is made to the step 105, where the foreign particle detection signal $S3(x)$ is obtained. Also, if at the step 108, the reticle 73 is not moved in Y direction, the foreign particle detection for the reticle 73 is terminated.

In the present embodiment, the sensitivity correction attributable to the transmittance of the pellicle 75 is effected after foreign particle detection, but it is also possible to effect similar correction during foreign particle detection. Thus, the present invention is not restricted to the above-described embodiments, but can assume various constructions without departing from the gist of the invention.

A case where the detected foreign particle is indicated will now be described as a fourth embodiment.

Figure 12:
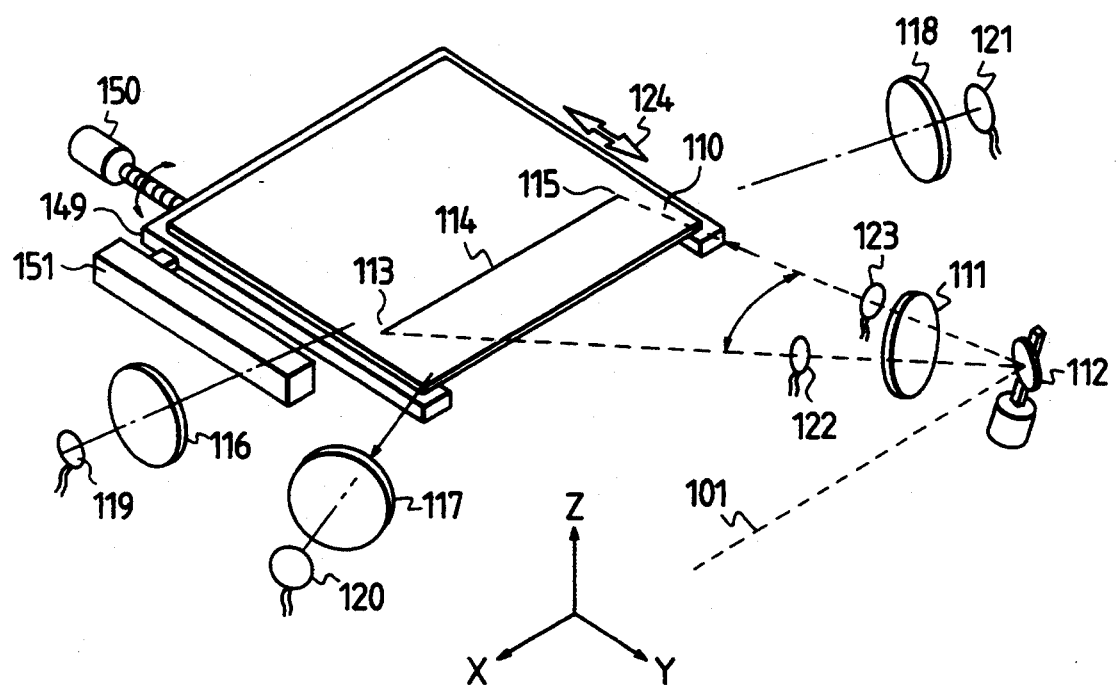
FIG. 12 schematically shows a foreign particle inspecting apparatus to illustrate a fourth embodiment of the present invention.

The number and size of foreign particles detected by the foreign particle inspecting apparatus as previously described are indicated in a map (distribution graph). The indicating method is not restricted to the apparatuses as shown in FIGS. 1 and 9, but here, a description will be given of a case where foreign particles detected by the foreign particle inspecting apparatus of FIG. 12 are indicated. FIG. 12 schematically shows a foreign particle inspecting apparatus to illustrate the indicating method of the present invention.

A laser beam 101 emitted from a light source, not shown, scans an object 110 to be inspected (such as a reticle or a wafer formed with a predetermined pattern) in X direction by a scanner 112 (such as a polygon mirror or a galvano mirror) as beam scanning means. At this time, the scanning laser beam 101 has its beam diameter changed into any beam diameter by a condensing optical system 111 for irradiation such as a condensing lens, whereafter it is stopped down into a spot light and is obliquely incident on the object 110 to be inspected. The starting point and terminal point of the scanning of the laser beam 101 scanned by the scanner 112 are detected by photoelectric detectors 122 and 123 for position detection. The object 110 to be inspected is placed on a stage 149, which is movable in a direction 124 (Y direction) substantially orthogonal to the scanning direction of the laser beam 101 by driving means 150 such as a motor. Thereby, the whole surface of the object 110 to be inspected becomes inspectable. Movement amount measuring means 151 such as a linear encoder is provided on the stage 149, and can measure the irradiated position on the object 110 to be inspected in Y direction.

Photoelectric elements 119, 120 and 121 are disposed so as to receive scattered light from irradiated portions 113–115 by the laser beam 101, from respective different spatial directions. The scattered light is condensed on the light receiving surfaces of these photoelectric elements 119, 120 and 121 by condensing lenses 116, 117 and 118, respectively. In order to reduce the influence of diffracted light from the pattern of the object 110 to be inspected, the optical axes of the condensing lenses 116, 117 and 118 are disposed so as to be oblique with respect to XY plane. The arrangement of the light receiving elements is determined so as not to receive the scattered light from the pattern edge at the same time.

Figure 13:
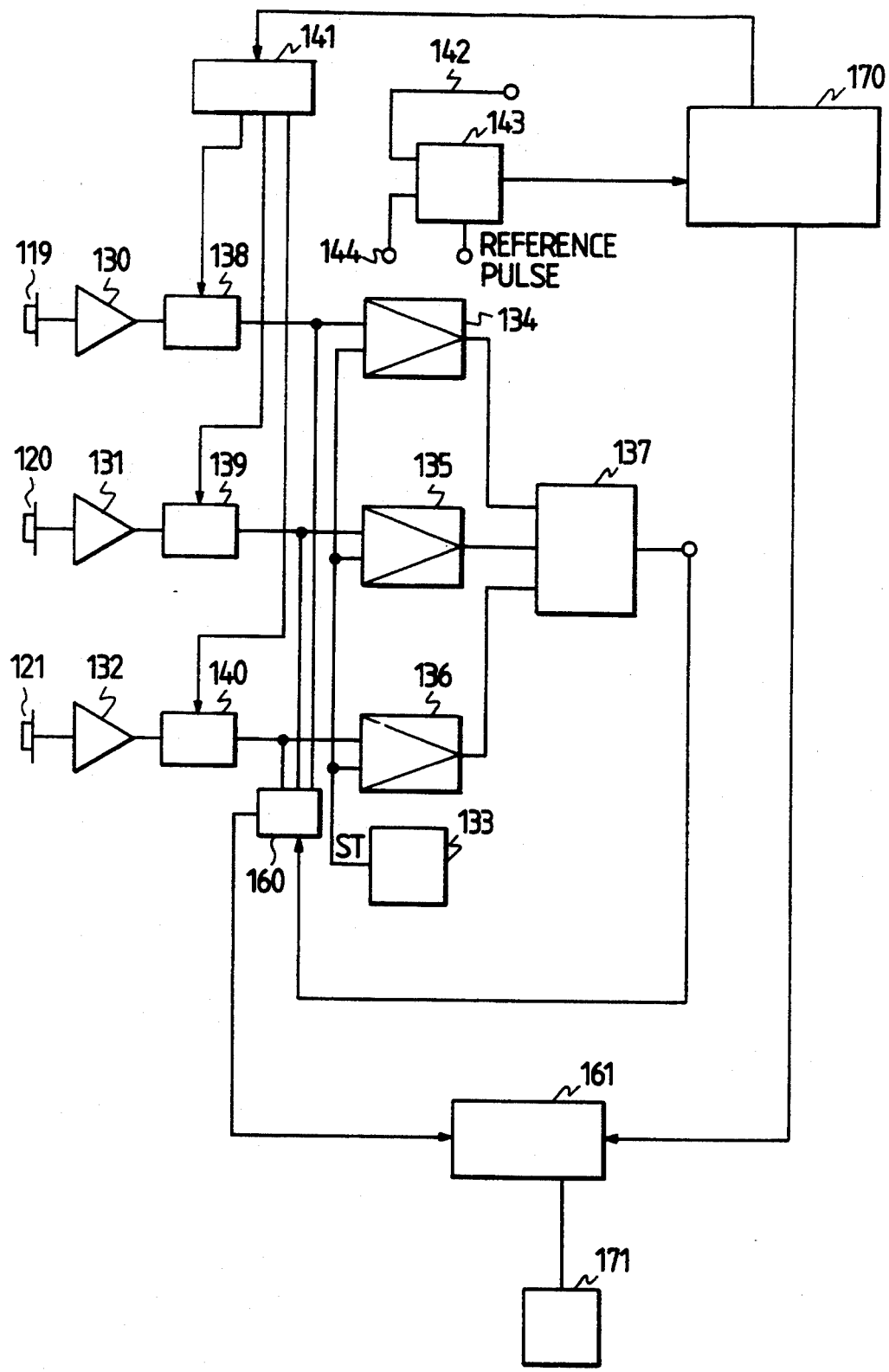
FIG. 13 is a block diagram showing the signal processing circuit of the apparatus of FIG. 1.

The signal processing by the present embodiment will now be described with reference to FIG. 13.

Photoelectric signals from the photoelectric elements 119, 120 and 121 are amplified by amplifiers 130, 131 and 132, respectively. The output signals of the amplifiers 130, 131 and 132 have their differences from a reference signal ST from a reference signal generator 133 taken by comparators 134, 135 and 136, respectively. A logic circuit 137 effects, for example, the calculation of the logical product of the outputs of the comparators to thereby discriminate between a foreign particle and a circuit pattern. Scattered light from a foreign particle enters all of the light receiving elements 119, 120 and 121, and scattered light from the pattern edge enters a particular photoelectric element. Accordingly, the logic circuit 137 outputs a predetermined foreign particle detection signal when all of the photoelectric elements output sufficient photoelectric signals. Also, the location of the foreign particle on the object to be inspected is found on the basis of the measured value by movement amount measuring means 151 (FIG. 12) and the scanning position of the laser beam 101.

Here, measuring means 143 starts the counting of a reference pulse with a signal from a photoelectric element 122 for position measurement (FIG. 12) as a start signal 142, and stops the counting with a signal from a photoelectric element 123 (FIG. 12) as a stop signal 144. The pulse number counted during this period is calculated by main control means 170 and the position of the spot by the laser beam 101 in X direction is determined. This spot position information is input to a memory 161.

Also, the photoelectric signals of the light receiving elements 119, 120 and 121 differ in magnitude from one another depending on the location of the foreign particle on the object 110 to be inspected. That is, the magnitude relation between the signals differs depending on the positional relation between the location of the foreign particle and the light receiving elements (depending on the distance between the foreign particle and the light receiving elements). So, variable amplifiers (VCAs) 138, 139 and 140 are provided forwardly of the amplifiers 130, 131 and 132, respectively, to thereby vary the gains. A controller 141 receives as an input from the main control means 170 the scanning position of the spot by the laser beam 101 in X direction, and controls the gains of the respective variable amplifiers in conformity with the disposition of the photoelectric elements 119, 120 and 121 relative to the scanning position of the spot light. Thereby, a signal depending on only the size of the foreign particle is obtained irrespective of the location of the foreign particle. The thus corrected signal (foreign particle size signal) is input to a comparator and is also input to a size discriminator 160. The size discriminator 160 outputs the maximum value of the signals from the three light receiving elements as the size information of the foreign particle to a memory 161. Here, the detection signal from the logical product circuit 137 is input to the size discriminator 160, and the maximum value when the detection signal is output (the maximum value of the signals from the three light receiving elements) is input to the memory 161.

In the present apparatus, the resolving power of the XY coordinates value is finally set to 1 mm, and the number and sizes of foreign particles are detected for each 1 mm square area on the object 110 to be inspected. The detected number and sizes of the foreign particles are displayed on a display device 171.

Figure 14:
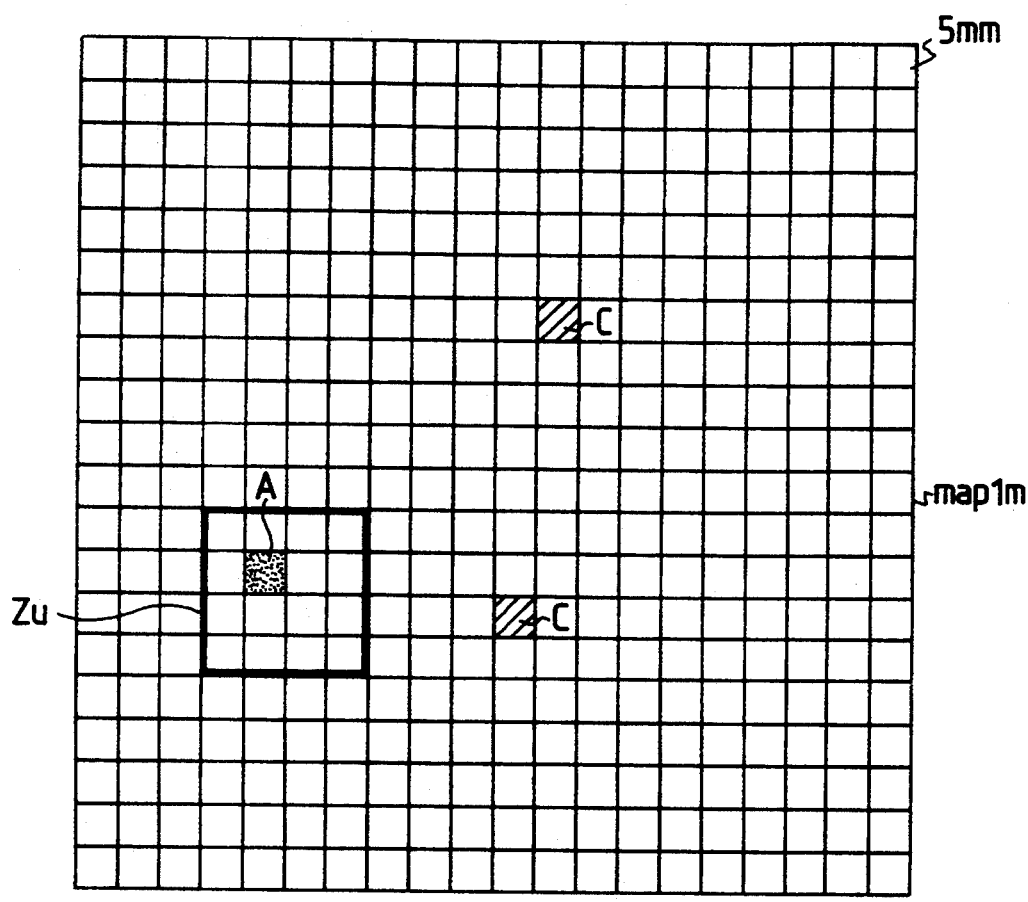
FIG. 14 shows a foreign particle data indicating method according to the fourth embodiment of the present invention.
Figure 15:
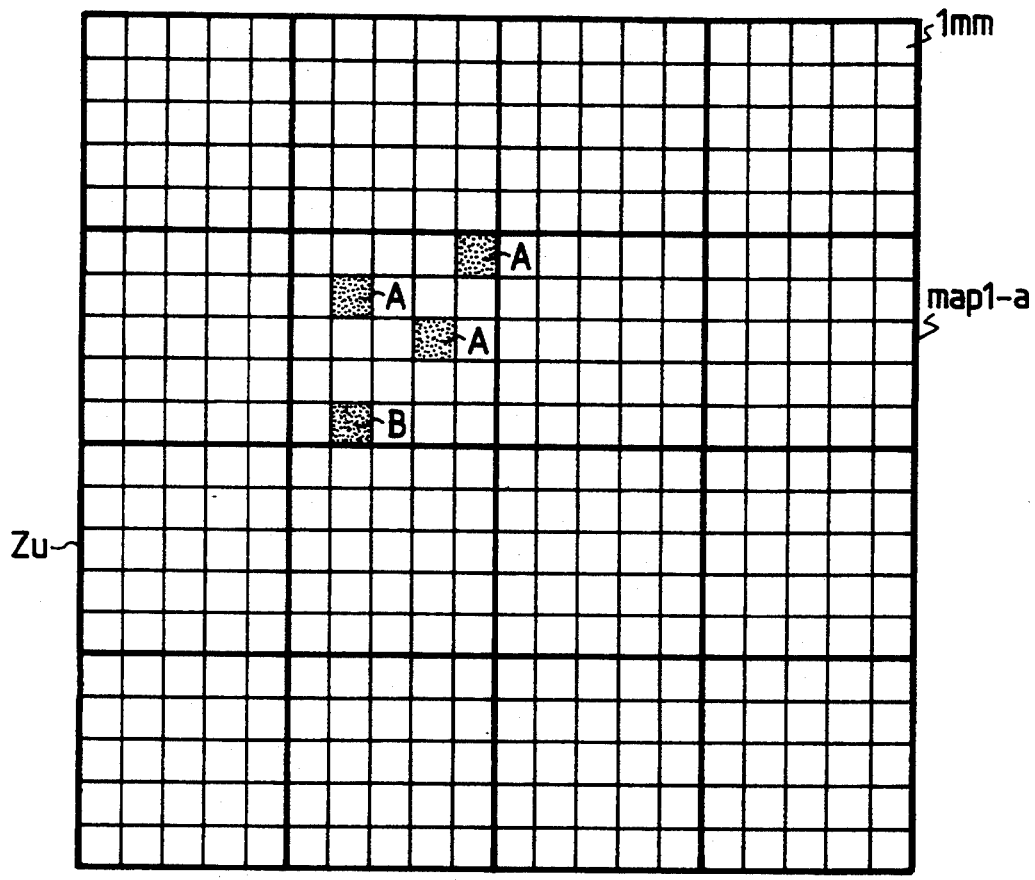
FIG. 15 shows the manner in which the indication of FIG. 14 is partially enlarged.
Figure 16:
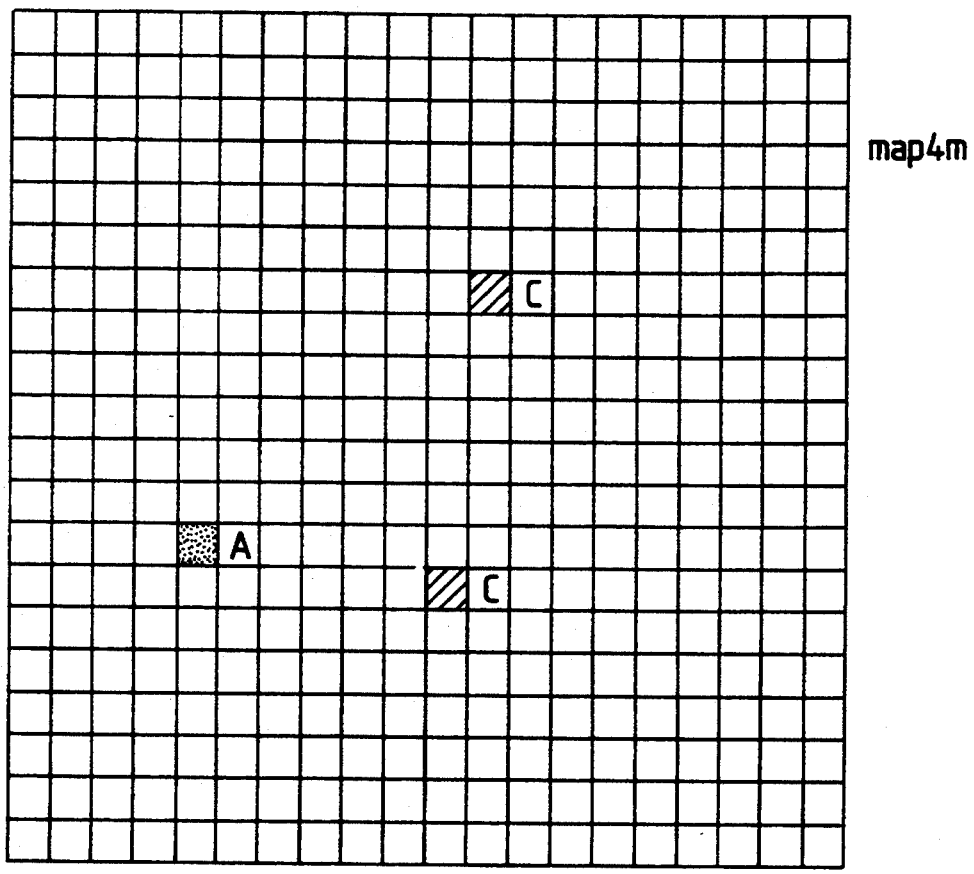
FIG. 16 shows an example of the conventional foreign particle data indicating method.

A description will now be given of the display of the locations and sizes of the foreign particles detected by the apparatus of FIG. 12. FIGS. 14 and 15 show the manner in which the foreign particles detected by the apparatus of FIG. 12 are map-indicated. In the present embodiment, the form of indication is such that the switching of the indication is possible with respect to two cases, i.e., a case where indication is made for each 5 mm square and a case where indication is made for each 1 mm square. FIG. 14 shows a case where indication is made with 5 mm square as a unit, and FIG. 15 shows a case where indication is made with 1 mm square as a unit. In the present embodiment, 1 mm square is the maximum indication unit.

The map1m of FIG. 14 indicates the locations and sizes of the foreign particles detected by the apparatus of FIG. 12. The size of each section of the map1m shows an area of a size of 5 mm square on the surface to be inspected, and this 5 mm square is a unit. 5 mm square being a unit is to make such a design that the largest foreign particle in 5 mm square is indicated.

Now, under the map1m, the numbers of foreign particles on the object to be inspected corresponding to the areas indicated in the map1m are indicated by ranks by an indicating portion 1. In the indicating portion 1, foreign particles are indicated with 5 mm square as a unit. In an indicating portion 2 (in parentheses), the total number of foreign particles existing in the whole area (inspectable area) on the object to be inspected is indicated by ranks, and in the indicating portion 2, foreign particles are indicated with 1 mm square as a unit.

In the present embodiment, ranks A, B and C are indicated in the order of greater sizes, and in the map1m, there is shown a state in which a foreign particle of rank A and two foreign particles of rank C have been detected.

As previously described, in the apparatus of FIG. 12, the detection of foreign particles is possible with 1 mm square as the resolving power (inspection unit), and each section (5 mm square) of the map1m of FIG. 14 includes twenty-five inspection units (1 mm). Accordingly, there is the possibility that foreign particles of different sizes may exist in one such section. As previously noted, the largest foreign particle in one section is indicated and therefore, small foreign particles are not indicated. However, by comparing the two numbers in the indicating portion 1 and the indicating portion 2, the presence of foreign particles of different sizes (small foreign particles) in one section (5 mm square) can be presumed easily.

In the present embodiment, a predetermined portion (e.g. an area Zu) in the display of FIG. 14 can be designated and the designated area Zu can be partly enlarged and indicated. The manner in which this area Zu is enlargedly map-indicated is shown in FIG. 15. In FIG. 15, the area Zu of FIG. 14 is only enlargedly indicated and the positional relations between foreign particles do not differ. The size of each section of the map1-a of FIG. 15 shows an area of a size of 1 mm square on the surface to be inspected, and foreign particles are map-indicated with 1 mm square as a unit. Here, the presence of the foreign particles hidden in the map of FIG. 14 can be confirmed. In the map1-a, there is shown a state in which three foreign particles of rank A and a foreign particle of rank B have been detected.

Now, under the map1-a, as in FIG. 15, the numbers of foreign particles in the indicating area are indicated by ranks in an indicating portion 1-a with a section (1 mm square) in the indicating area as a unit. Also, the number of foreign particles on the whole surface to be inspected is indicated by ranks in an indicating portion 2-a (in parentheses) with 1 mm square as a unit.

In FIGS. 14 and 15, the numbers in the indicating portions 2 and 2-a are numbers with 1 mm square in the whole inspection area as a unit. In the indicating portion 1-a of FIG. 15, the numbers of foreign particles in the indicating area are indicated and therefore, the numbers therein differ in spite of being indicated in the same unit area as the indicating portion 2-a. It is also possible that the numbers in the indicating portion 2-a are regarded as numbers of 1 mm square unit in the indicating area. Thereby, where the display of 5 mm square unit of FIG. 14 is enlargedly indicated, for example, at 3 mm square unit, the presence of small foreign particles in the indicating area being enlargedly indicated can be confirmed. Also, in the above-described embodiment, the minimum indication unit is 1 mm square, but the minimum indication unit may be determined to any size, and the minimum indication unit may be made changeable.

Also, it is to be understood that the number of foreign particles is recorded on a file, but the design may be such that when the number of foreign particles reaches a predetermined number (e.g. 3,000 or more)i, the recording on the file is not effected.

The above-described indicating method is also applicable to a foreign particle inspecting apparatus for inspecting a reticle through a pellicle and an apparatus for inspecting a pellicle.

The above-described embodiment is an embodiment of the present invention and is not restrictive.

What is claimed is:

1. A foreign particle inspecting method in which a polarized beam is applied to a surface to be inspected through a light transmitting member mounted thereon, in which scattered light from a foreign particle on the surface to be inspected is received by a light receiving device through said light transmitting member, and in which said foreign particle is discriminated based on a detection signal from said light receiving device, including:

providing first information as to transmittance of said light transmitting member for said polarized beam conforming to the angle of incidence of said polarized beam onto said light transmitting member;

providing second information as to transmittance of said light transmitting member for a non-polarized beam conforming to the angle of incidence of said non-polarized beam onto said light transmitting member; and correcting said detection signal in conformity with the transmittance for the polarized beam and the transmittance for the non-polarized beam.

2. The method of claim 1, wherein said non-polarized beam is light of a wavelength substantially equal to that of said polarized beam.

3. The method of claim 1, wherein said first information is provided by actually measuring the transmittance of said light transmitting member for said polarized beam conforming to the angle of incidence of said polarized beam onto said light transmitting member, and said second information is provided by actually measuring the transmittance of said light transmitting member for said non-polarized beam conforming to the angle of incidence of said non-polarized beam onto said light transmitting member.

4. The method of claim 1, wherein one of said first information and said second information is provided by actually measuring transmittance of said light transmitting member, and the other of said first information and said second information is found based on the actually measured transmittance.

5. A foreign particle inspecting apparatus for inspecting a foreign particle on a surface to be inspected, including:

a portion for applying a polarized beam to said surface to be inspected through a light transmitting member mounted thereon;

a light receiving portion for receiving scattered light from a foreign particle on said surface to be inspected through said light transmitting member and outputting a detection signal;

a discriminating portion for discriminating said foreign particle based on the detection signal from said light receiving portion;

a first measuring portion for actually measuring the transmittance of said light transmitting member for said polarized beam conforming to the angle of incidence of said polarized beam onto said light transmitting member;

a second measuring portion for actually measuring the transmittance of said light transmitting member for a non-polarized beam conforming to the angle of incidence of said non-polarized beam onto said light transmitting member; and a correcting portion for correcting said detection signal in conformity with the transmittance of said light transmitting member for said polarized beam at the angle of incidence of said polarized beam onto said light transmitting member and the transmittance of said light transmitting member for said non-polarized beam at the angle of incidence of said non-polarized beam, which is equal to an angle of emergence of said scattered light from said light transmitting member.

6. The apparatus of claim 5, wherein said second measuring portion has a member for changing said polarized beam into non-polarized light.

7. The apparatus of claim 5, further including a calculating portion for calculating the transmittance for said polarized beam conforming to said angle of incidence and the transmittance for said non-polarized beam conforming to said angle of emergence by interpolation.

8. A foreign particle inspecting method in which a polarized beam is applied to a surface to be inspected through a light transmitting member mounted thereon, in which scattered light from a foreign particle on the surface to be inspected is received by a light receiving device through said light transmitting member, and in which said foreign particle is discriminated based on a detection signal from said light receiving device, including:

providing first information as to transmittance of said light transmitting member for said polarized beam;

providing second information as to transmittance of said light transmitting member for a non-polarized beam; and correcting said detection signal based on the first information as to the transmittance for the polarized beam and the second information as to the transmittance for the non-polarized beam.

9. A foreign particle inspecting method in which a surface of a substrate to be inspected having mounted thereon a frame with light transmitting thin film attached thereto is scanned by incident light, and in which a foreign particle adhering to said substrate to be inspected is detected based on a signal obtained by converting light information created from said substrate to be inspected, said method using:

a reference substrate with a surface having a standard particle attached thereto covered with a light transmitting reference thin film mounted on a frame, and transmittance measuring means for applying first light to said reference thin film and measuring the reflectance of said reference thin film to thereby measure the transmittance of said reference thin film, scanning means for scanning the surface of said substrate to be inspected by second light, light receiving means for receiving light information created from said substrate to be inspected and outputting a detection signal, and foreign particle detecting means for detecting said foreign particle based on said detection signal; said method including:

a first step of measuring the transmittance of said reference thin film covering the surface of said reference substrate for said first light by the use of said transmittance measuring means;

a second step of detecting scattered light from said standard particle attached to the surface of said reference substrate through said reference thin film by the use of said scanning means, said light receiving means, and said foreign particle detecting means; and a third step of correcting said detection signal based on the transmittance obtained in said first step and the scattered light detected in said second step.

10. The method of claim 9, wherein said third step includes:

a fourth step of finding a sensitivity correction value obtained by a standard signal predetermined regarding said standard particle being divided by the detection signal output from said light receiving means of said foreign particle detecting means in said second step;

a fifth step of measuring the transmittance of said thin film covering the surface of said substrate to be inspected for said first light by the use of said transmittance measuring means; and wherein the detection signal is corrected based on the transmittance of said reference thin film measured in said first step, said sensitivity correction value found in said fourth step, and the transmittance of said thin film measured in said fifth step.

11. A foreign particle inspecting apparatus in which a surface of a substrate to be inspected having mounted thereon a frame having light transmitting thin film attached thereto is scanned by incident light, and in which a foreign particle adhering to said substrate to be inspected is detected based on a signal obtained by converting light information created from said substrate to be inspected, including:

a portion for applying first light to a reference thin film;

a first light receiving portion for detecting reflected light from said reference thin film;

a transmittance measuring portion for measuring the reflectance of thin film to thereby measure the transmittance of thin film;

a detecting portion having a scanning portion for scanning said substrate to be inspected by second light and a second light receiving portion for converting light received from said substrate to be inspected into an output signal;

a first memory portion for memorizing the transmittance of said reference thin film measured by said transmittance measuring portion;

a second memory portion for memorizing a predetermined sensitivity correction value; and a correcting portion for correcting said output signal from said detecting portion based on said sensitivity correction value memorized in said second memory portion, the transmittance of said reference thin film memorized in said first memory portion, and the transmittance of the thin film covering the surface of said substrate to be inspected measured by said transmittance measuring portion.

12. A method of indicating the number of foreign particles of different sizes and the positions of such foreign particles on an area of an object to be inspected, comprising:

providing a map of said area divided into sections of a predetermined size;

indicating (a), for each section, the largest foreign particle that is present;

indicating (b), based on said indicating (a), the number of foreign particles of different sizes present on said map; and indicating (c), for at least one section of said map, the number of foreign particles of different sizes present in said at least one section;

wherein all of the indicating (a), (b), and (c) is performed concurrently.

13. The method of claim 12, wherein said indicating (c) includes forming another map of said at least one section divided into sub-sections of a predetermined size and indicating, for each of said sub-sections, the largest foreign particle that is present.

14. A foreign particle inspecting method in which a surface of a substrate to be inspected having mounted thereon a frame with a light transmitting thin film attached thereto is scanned by incident light, and in which a foreign particle adhering to said substrate to be inspected is detected based on a signal obtained by converting light information created from said substrate to be inspected, said method comprising:

providing a reference substrate with a surface having a standard particle attached thereto covered with a light transmitting reference thin film mounted on a frame;

measuring the transmittance of the reference thin film for an incident light beam and for a scattered light beam from said reference substrate;

scanning said reference substrate, with said standard particle adhered thereto, with an incident light beam transmitted through said reference thin film and detecting scattered light from said standard particle;

measuring the transmittance of the thin film covering the substrate to be inspected for an incident light beam and for a scattered light beam from said substrate to be inspected;

scanning said substrate to be inspected with a light beam transmitted through said thin film covering said substrate to be inspected, detecting scattered light from a foreign particle adhered to said substrate to be inspected, and producing an output signal from the detected scattered light; and correcting said output signal based on the measured transmittance of said reference thin film, the measured transmittance of said thin film covering said substrate to be inspected, and the detected scattered light from said standard particle.

* * * * *